United States Patent [19]
Audia et al.

[11] Patent Number: 5,861,408
[45] Date of Patent: Jan. 19, 1999

[54] TETRAHYDRO-BETA-CARBOLINES

[75] Inventors: James E. Audia, Indianapolis, Ind.; Stephen Richard Baker, Surrey, England; Jesus Ezquerra Carrera, Madrid, Spain; Carlos Lamas Peteira, Madrid, Spain; Concepcion Pedregal Tercero, Madrid, Spain

[73] Assignee: Eli Lilly and Company, Indianapolis, Ind.

[21] Appl. No.: 835,452

[22] Filed: Apr. 8, 1997

Related U.S. Application Data

[62] Division of Ser. No. 444,449, May 19, 1995, Pat. No. 5,643,916.

[51] Int. Cl.⁶ .................. A61K 31/44; C07D 471/04; C07D 471/10
[52] U.S. Cl. ................... 514/278; 546/49; 546/70
[58] Field of Search .................. 546/86, 87, 49, 546/70, 18; 514/278

[56] References Cited

U.S. PATENT DOCUMENTS

| | | | |
|---|---|---|---|
| 5,300,645 | 4/1994 | Audia et al. | 546/49 |
| 5,488,053 | 1/1996 | Audia et al. | 514/280 |
| 5,538,981 | 7/1996 | Audia et al. | 514/292 |
| 5,629,317 | 5/1997 | Audia et al. | 514/278 |

FOREIGN PATENT DOCUMENTS 0 466 548  6/1991  France ........................ 471/4

OTHER PUBLICATIONS

Derwent Abstract 03884Y/03 25.06.75 BE–843–215.
Derwent Abstract 68225 c/39 05.02.79 EP—15–786.
Derwent Abstract 84–115276/19 29.10.82 DE–3240–514–A.
Derwent Abstract 40991 14.4.67 US/3,840,637.
Dubois, et al., *J. Org. Chem.*, 59, 434–441 (1994).
Legters, et al., *Rccl. Trav. Chim. Pays–Bas,* 111, 16–21 (1992).
Sato, K. And Kozikowski, A. P., *Tetrahedron Letters,* 30:31., 4073–4076, (1989).
Shima, et al., *Chem. Pharm. Bull.,* 38:2, 564–566 (1990).

*Primary Examiner*—Alan L. Rotman
*Attorney, Agent, or Firm*—Arleen Palmberg

[57] ABSTRACT

The present invention provides novel tetrahydro-beta-carboline compounds having useful central nervous system activity. Further, there is provided tetrahydro-beta-carboline related compounds which are useful intermediates and have beneficial central nervous system activity. The invention provides formulations and methods for using the novel tetrahydro-beta-carboline and related compounds. Such compounds are particularly useful for the modulation of a 5-HT$_{2B}$ receptor.

5 Claims, No Drawings

TETRAHYDRO-BETA-CARBOLINES

This application is a division of application Ser. No. 08/444,449 filed May 19, 1995, now U.S. Pat. No. 5,643,916.

FIELD OF THE INVENTION

The present invention relates to the field of organic chemistry. The invention provides novel tetrahydro-beta-carboline compounds and intermediates with a high affinity for the 5-HT$_{2B}$ receptor.

BACKGROUND OF THE INVENTION

Blocking serotonin receptors has been shown to result in a number of beneficial pharmacological effects, including reduction in disease states such as hypertension, depression, anxiety, and the like; see U.S. Pat. No. 5,141,944. Nelson et al., *Psychopharmacology and Biochemistry of Neurotransmitter Receptors*, eds. H. I. Yamamura et al., Elsevier/North Holland Inc., p 325, have confirmed that there are multiple serotonin recognition sites. The general class of serotonin receptors are referred to as the 5-HT receptors. Specific 5-HT receptor sites include 5-HT$_{1A}$, 5-HT$_{1B}$, 5-HT$_{1D}$, 5-HT$_{2A}$, 5-HT$_{2B}$, 5-HT$_{2C}$, 5-HT$_3$, and 5-HT$_4$ sites. Each of these receptors mediates certain physiological effects. See Leonard, B. E., *International Clinical Psychopharmacology*, 7:13–21 (1992).

This invention provides new compounds and a method for using such compounds which are active at the 5-HT$_{2B}$ receptor to treat or prevent 5-HT$_{2B}$ related conditions. Further, this invention provides a method for selectively blocking the 5-HT$_{2B}$ receptor. Additionally, this invention provides a method for blocking human 5-HT$_{2B}$ receptors.

This invention provides a group of compounds which are 5HT$_{2B}$ receptor antagonists. Applicants have discovered that such compounds are potent competitive inhibitors of serotonin-induced contraction of the colon. Thus, this invention provides compounds which can act to normalize gastrointestinal motility and be useful in the treatment of Functional Bowel Disorders.

Further, it has been discovered the 5-HT$_{2B}$ receptor is localized in the rat lung, stomach fundus, uterus, bladder, and colon. Interesting areas of 5-HT$_{2B}$ receptor localization in the human include but are not limited to the brain and blood vessels. Thus, conditions which can be treated using a compound which modulates a 5-HT$_{2B}$ receptor includes, for example, psychosis, depression, anxiety disorders, uterine diseases such as endometriosis, fibrosis, and other abnormal uterine contractivity, panic attack, migraine, eating disorders, seasonal affective disorder, consumption disorders, cardiovascular conditions, such as thrombosis, hypertension, angina, vasospasm, and other vascular occlusive diseases, incontinence, bladder dysfunction, respiratory/airway disorders including asthma, and the like.

SUMMARY OF THE INVENTION

This invention provides a group of novel compounds with 5-HT$_{2B}$ receptor activity. Additionally, the present compounds are useful tools to characterize the effects of the 5-HT$_{2B}$ receptor and to develop therapeutic agents based on 5-HT$_{2B}$ receptor modulation.

The present invention provides compounds of the Formula I

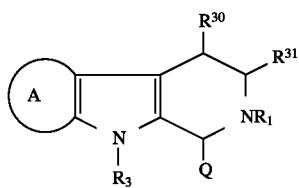

wherein

Q is selected from the group consisting of hydrogen, R$_{34}$, and (CHR$_2$)R$_4$;

R$_{34}$ is spiro-bicyclic, substituted spiro-bicyclic, bicyclic or substituted bicyclic;

R$_1$ is hydrogen or C$_1$–C$_3$ alkyl;

R$_2$ is hydrogen or C$_1$–C$_6$ alkyl;

R$_3$ is hydrogen or C$_1$–C$_3$ alkyl;

R$_4$ is C$_5$–C$_8$ cycloalkyl, substituted C$_5$–C$_8$ cycloalkyl, C$_5$–C$_8$ cycloalkenyl, substituted C$_5$–C$_8$ cycloalkenyl, bicyclic or substituted bicyclic;

A is selected from the group consisting of

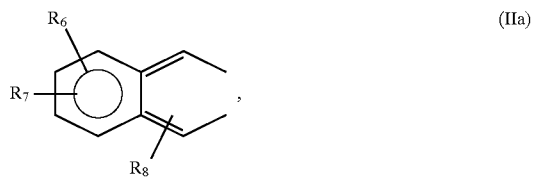 (IIa)

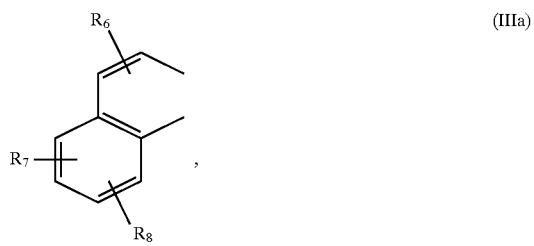 (IIIa)

and

 (IVa)

wherein

R$_6$ and R$_7$ are, independently, hydrogen, C$_1$–C$_6$ alkyl, C$_2$–C$_6$ alkenyl, halo, halo(C$_1$–C$_6$)alkyl, halo(C$_2$–C$_6$) alkenyl, COR$_5$, C$_1$–C$_{10}$ alkanoyl, CO$_2$R$_5$', (C$_1$–C$_6$ alkyl)$_m$amino, NO$_2$, —SR$_5$, or OR$_5$;

m is 1 or 2;

R$_5$ is independently hydrogen or C$_1$–C$_4$ alkyl;

R$_5'$ is C$_1$–C$_4$ alkyl;

R$_8$ is independently selected from the group consisting of an R$_6$ group, substituted C$_3$–C$_8$ cycloalkyl, C$_3$–C$_8$ cycloalkyl, C$_3$–C$_8$ cycloalkyl-(C$_1$–C$_3$)alkyl, C$_5$–C$_8$ cycloalkenyl, substituted C$_5$–C$_8$ cycloalkenyl, C$_5$–C$_8$ cycloalkenyl-(C$_1$–C$_3$)alkyl, C$_7$–C$_{16}$ arylalkyl; or R$_6$ and R$_7$ together with the carbon atoms of group A form a 5- to 8-member carbon ring;

R$^{30}$ and R$^{31}$ join to form a 3 to 8 member carbon ring; or

R$^{30}$ and R$^{31}$ are independently selected from the group consisting of C$_1$–C$_6$ alkyl and C$_2$–C$_6$ alkenyl; or a pharmaceutically acceptable salt or solvate thereof. This invention provides compounds of Formula II

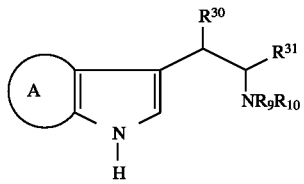

A is selected from the group consisting of

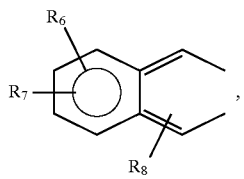   (IIa)

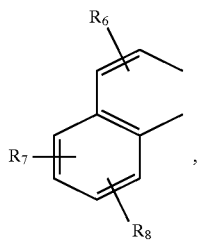   (IIIa)

and

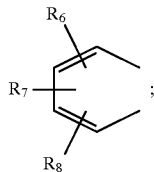   (IVa)

wherein $R_6$ and $R_7$ are, independently, hydrogen, $C_1$–$C_6$ alkyl, $C_2$–$C_6$ alkenyl, halo, halo($C_1$–$C_6$)alkyl, halo($C_2$–$C_6$) alkenyl, $COR_5$, $C_1$–$C_{10}$ alkanoyl, $CO_2R_{5'}$, ($C_1$–$C_6$ alkyl)$_m$amino, $NO_2$, —$SR_5$, or $OR_5$;

m is 1 or 2;

$R_8$ is selected from the group consisting of hydrogen, $C_1$–$C_6$ alkyl, $C_2$–$C_6$ alkenyl, halo, halo($C_2$–$C_6$)alkyl, halo($C_1$–$C_6$)alkenyl, $COR_5$, $C_1$–$C_{10}$ alkanoyl, $CO_2R_{5'}$, ($C_1$–$C_6$ alkyl)$_m$amino, $NO_2$, —$SR_5$, $OR_5$, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl, substituted $C_5$–$C_8$ cycloalkenyl, $C_5$–$C_8$ cycloalkenyl-($C_1$–$C_3$)alkyl, and $C_7$–$C_{16}$ arylalkyl;

$R_5$ is independently hydrogen or $C_1$–$C_4$ alkyl;

$R_{5'}$ is $C_1$–$C_4$ alkyl;

$R_6$ and $R_7$ together with the carbon atoms of group A form a 5- to 8-member carbon ring;

$R_9$ and $R_{10}$ are independently selected from the group consisting of hydrogen, $C_1$–$C_6$ alkyl, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$)alkyl, $C_7$–$C_{16}$ arylalkyl;

$R_{11}$ is selected from the group consisting of $C_1$–$C_4$ alkyl, $OR_{5'}$, fluoro, bromo, iodo, and chloro;

$R^{30}$ and $R^{31}$ join to form a 3 to 8 member carbon ring; or $R^{30}$ and $R^{31}$ are independently selected from the group consisting of $C_1$–$C_6$ alkyl and $C_2$–$C_6$ alkenyl; or a pharmaceutically acceptable salt or solvate thereof.

DETAILED DESCRIPTION OF THE INVENTION

The term "treating" as used herein includes prophylaxis of the named physical and/or mental condition or amelioration or elimination of the developed physical and/or mental condition once it has been established.

The terms "$C_1$–$C_n$ alkyl" wherein n=2–10, as used herein, represent a branched or linear alkyl group having from one to the specified number of carbon atoms. Typical $C_1$–$C_6$ alkyl groups include methyl, ethyl, n-propyl, iso-propyl, butyl, iso-butyl, sec-butyl, tert-butyl, pentyl, hexyl and the like.

The terms "$C_2$–$C_n$ alkenyl" wherein n=3–10, as used herein, represents an olefinically unsaturated branched or linear group having from 2 to 10 carbon atoms and at least one double bond. The groups can be branched or straight chain. Examples of such groups include 1-propenyl, 2-propenyl(—$CH_2$—$CH$=$CH_2$), 1,3-butadienyl(—$CH$=$CHCH$=$CH_2$), 1-butenyl(—$CH$=$CHCH_2CH_3$), hexenyl, pentenyl, and the like.

The terms "halide", "halogen", and "halo" include fluorine, chlorine, bromine, and iodine. The preferred halogen is chlorine.

The terms "halo($C_1$–$C_6$)alkyl" and "halo($C_2$–$C_6$)alkenyl" refer to alkyl or alkenyl substituents having one or more independently selected halo atoms attached at one or more available carbon atoms. These terms include chloromethyl, bromoethyl, trifluoroethyl, trifluoromethyl, trifluoroethylenyl, 3-bromopropyl, 3-bromo-1-propenyl, 2-bromopropyl, 2-bromo-1-propenyl, 3-chlorobutyl, 3-chloro-2-butenyl, 2,3-dichlorobutyl, chloroethylenyl, 5-fluoro-3-pentenyl, 3-chloro-2-bromo-5-hexenyl, 3-chloro-2-bromobutyl, trichloromethyl, dichloroethyl, 1,4-dichlorobutyl, 3-bromopentyl, 1,3-dichlorobutyl, 1,1-dichloropropyl, and the like. More preferred halo-($C_1$–$C_6$) alkyl groups are trichloromethyl, trichloroethyl, and trifluoromethyl. The most preferred halo-($C_1$–$C_6$)alkyl is trifluoromethyl.

The term "$C_1$–$C_{10}$ alkanoyl" represents a group of the formula $C(O)(C_1$–$C_9)$ alkyl. Typical $C_1$–$C_{10}$ alkanoyl groups include acetyl, propanoyl, butanoyl, and the like.

The term "($C_1$–$C_6$ alkyl)$_m$ amino" wherein m=1–2; refers to either a mono- or a dialkylamino group in which the alkyl portion of the group may be straight or branched. Examples of such groups are methylamino, dimethylamino, ethylamino, diethylamino, 2-propylamino, 1-propylamino, di(n-propyl)amino, di(iso-propyl)amino, methyl-n-propylamino, t-butylamino, and the like.

The term "$C_3$–$C_n$ cycloalkyl" wherein n=4–8, represents cyclopropyl, cyclobutyl, cyclopentyl, cyclohexyl, cycloheptyl, and cyclooctyl.

The term "substituted ($C_5$–$C_n$)cycloalkyl" refers to a cycloalkyl group as described supra wherein the cycloalkyl group may be substituted with from one to four substituents independently selected from the group consisting of hydrogen, $C_1$–$C_6$ alkyl, $NO_2$, halo, halo($C_1$–$C_6$)alkyl, halo ($C_2$–$C_6$)alkenyl, $C_2$–$C_6$ alkenyl, $CO_2R_5$, ($C_1$–$C_6$ alkyl)$_m$ amino, —$SR_5$, and $OR_5$.

The term "$C_3$–$C_8$ cycloalkyl-($C_1$–$C_3$)alkyl" represents a linear alkyl group substituted at a terminal carbon with a $C_3$–$C_8$ cycloalkyl group. Typical cycloalkylalkyl groups include cyclohexylethyl, cyclohexylmethyl, 3-cyclopentylpropyl, and the like.

The term "$C_5$–$C_8$ cycloalkenyl" represents an olefinically unsaturated ring having five to eight carbon atoms, eg., cyclohexadienyl, cyclohexenyl, cyclopentenyl, cycloheptenyl, cyclooctenyl, cyclohexadienyl, cycloheptadienyl, cyclooctatrienyl and the like.

The terms 'substituted phenyl' and "($C_5$–$C_8$) cycloalkenyl" refer to a phenyl or cycloalkenyl group as described supra wherein the group may be substituted with from one to four substituents independently selected from the group consisting of hydrogen, $C_1$–$C_6$ alkyl, $NO_2$, halo, halo($C_1$–$C_6$)alkyl, halo($C_2$–$C_6$)alkenyl, $C_2$–$C_6$ alkenyl, $COR_5$, $C_1$–$C_{10}$ alkanoyl, $C_7$–$C_{16}$ arylalkyl, $CO_2R_5$, ($C_1$–$C_6$ alkyl)$_m$ amino, —$SR_5$, and $OR_5$.

The terms 'phenyl-($C_1$–$C_3$)alkyl' and "$C_5$–$C_8$ cycloalkenyl-($C_1$–$C_3$)alkyl" represent a linear $C_1$–$C_3$ alkyl group substituted at a terminal carbon with phenyl or a $C_5$–$C_8$ cycloalkenyl group.

The term "aryl" represents phenyl or naphthyl. The aryl group can be unsubstituted or can have one or two substituents independently selected from the group consisting of $C_1$–$C_6$ alkyl, $C_3$–$C_8$ cycloalkyl, substituted $C_3$–$C_8$ cycloalkyl, $C_2$–$C_6$ alkenyl, $C_3$–$C_8$ cycloalkyl-($C_1$–$C_3$)alkyl, phenyl, $C_5$–$C_8$ cycloalkenyl, substituted $C_5$–$C_8$ cycloalkenyl, $C_5$–$C_8$ cycloalkenyl-($C_1$–$C_3$)alkyl, $COR_5$, $C_1$–$C_{10}$ alkanoyl, $OR_5$, and $C_7$–$C_{16}$ arylalkyl. The substituents may be located at any available position on the aryl ring.

The term "$C_7$–$C_{20}$ arylalkyl" represents an aryl-($C_1$–$C_{10}$) alkyl substituent wherein the alkyl group is linear, such as benzyl, phenethyl, 3-phenylpropyl, or phenyl-t-butyl; or branched. The alkyl portion bonds at the point of attachment to the parent molecule.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "unsaturated bicyclic" represents a stable bicyclic ring of 7 to 12 carbon atoms. The unsaturated bicyclic ring may be attached at any carbon atom which affords a stable structure. The unsaturated bicyclic ring may be substituted with from one to four substituents as defined for "substituted bicyclic" infra.

The general term "substituted bicyclic" refers to a bicyclic ring system with 4 substituents attached at any desired positions on the bicyclic ring system. The bicyclic substituents may be independently selected from the group consisting of hydrogen, $C_1$–$C_6$ alkyl, $NO_2$, halo, halo($C_1$–$C_6$)alkyl, halo($C_2$–$C_6$)alkenyl, $C_2$–$C_6$ alkenyl, $COR_5$, $C_1$–$C_{10}$ alkanoyl, $C_7$–$C_{16}$ arylalkyl, $CO_2R_5$, ($C_1$–$C_6$ alkyl)$_m$amino, —$SR_5$, and $OR_5$; wherein $R_5$ is defined supra. It is intended that the substituted bicyclic substituent may bond to the $CHR_2$ group through any available carbon atom in the bicyclic ring system. The term includes, but is not limited to compounds such as, 2-methyldicyclohexyl, 3-hydroxydicyclohexyl, benzocyclohexyl, benzocyclohexenyl, 2-methoxybenzocyclohexyl, 6-chlorobenzocyclohexenyl, 8-ethenylbenzocyclohexyl, and the like. The term "spiro-bicyclic" and "substituted spiro-bicyclic" refer to a bicyclic or substituted bicyclic (as defined supra.) directly attached to the carbon of the parent ring at Q. For illustration purposes, a spiro-bicyclic is attached as shown:

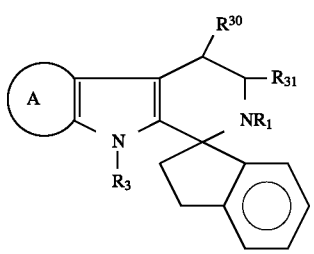

The term "naphthyl" refers to a naphthalene ring system substituent, as commonly used in organic chemistry. The naphthyl substituent may bond to the $CHR_2$ group through any available carbon atom in the naphthyl ring system. The term "substituted naphthyl" refers to a naphthyl ring system with 4 sustituents attached at any desired positions on the naphthyl ring system. The naphthyl substituents may be independently selected from the "substituted bicyclic" group supra.

The term "selective binding of a 5-$HT_{2B}$ receptor" refers to a method of binding the 5-$HT_{2B}$ receptor to a greater extent than it binds the 5-$HT_{2A}$ and/or 5-$HT_{2C}$ receptors.

The term "protic acid" refers to an acid having an acidic hydrogen. Preferred protic acids include hydrochloric acid, formic acid, perchloric acid, sulfuric acid, and phosphoric acid in an aqueous medium. The most preferred protic acids are hydrochloric acid, sulfuric acid, and formic acid.

The term "organic solvent" includes solvents containing carbon, such as halogenated hydrocarbons, ether, toluene, xylene, benzene, and tetrahydrofuran.

The term "agitate" includes such techniques as stirring, centrifugation, mixing, and other similar methods.

The term "aprotic solvent" refers to polar solvents of moderately high dielectric constant which do not contain an acidic hydrogen. Examples of common aprotic solvents are dimethyl sulfoxide (DMSO), dimethylformamide, sulfolane, tetrahydrofuran, diethyl ether, methyl-t-butyl ether, or 1,2-dimethoxyethane.

The term "protic solvent" refers to a solvent containing hydrogen that is attached to oxygen, and hence is appreciably acidic. Common protic solvents include such solvents as water, methanol, ethanol, 2-propanol, and 1-butanol.

The term "inert atmosphere" refers to reaction conditions in which the mixture is covered with a layer of inert gas such as nitrogen or argon.

Abbreviations used herein have their accepted meaning, unless stated otherwise. For example, "Me" and "Et" refer to methyl, ethyl respectively, and "t-Bu" refers to tertiary-butyl. The abbreviation "RT" refers to room temperature or ambient conditions unless indicated otherwise.

The term "ligand" refers to compounds that are bound by the 5-$HT_{2B}$ and/or 5-$HT_2$ receptor. Compounds useful as 5-$HT_{2B}$ selective ligands may be used to selectively occupy a 5-$HT_{2B}$ receptor site or may act as a selective agonist at a 5-$HT_{2B}$ receptor site.

The term "substantially pure" is intended to mean at least about 90 mole percent, more preferably at least about 95 mole percent, and most preferably at least about 98 mole percent of the desired enantiomer or stereoisomer is present compared to other possible configurations.

As used herein the term "functional bowel disorder" refers to a functional gastrointestinal disorder manifested by (1) abdominal pain and/or (2) symptoms of disturbed defecation (urgency, straining, feeling of incomplete evacuation, altered stool form [consistency] and altered bowel frequency/timing) and/or (3) bloating (distention). The term "functional bowel disorder" includes but is not limited to irritable bowel syndrome, hypermotility, ichlasia, hypertonic lower esophogeal sphincter, tachygastria, constipation, hypermotility associated with irritable bowel syndrome.

The formula (I), (II) and all compounds claimed herein can form acid addition salts with a wide variety of inorganic and organic acids. Typical acids which can be used include sulfuric, hydrochloric, hydrobromic, phosphoric, hypophosphoric, hydroiodic, sulfamic, citric, acetic, maleic, malic, succinic, tartaric, cinnamic, benzoic, ascorbic, mandelic, p-toluenesulfonic, benzenesulfonic, methanesulfonic, trifluoroacetic, hippuric and the like. The pharmaceutically acceptable acid addition salts of the Formula (I) and (II) compounds are especially preferred.

The compounds of the present invention are useful for modulating or blocking the 5-HT$_2$ receptor. Certain of the present compounds are preferred for that use. The following invention embodiments and compound characteristics listed in tabular form may be independently selected or combined to produce a variety of preferred compounds and embodiments of the invention. The following list of embodiments of this invention is in no way intended to limit the scope of this invention in any way.

A) $R_1$ is hydrogen;
B) $R_2$ is hydrogen or methyl;
C) $R_3$ is hydrogen or methyl;
D) $R_4$ is $C_5$–$C_8$ cycloalkenyl or substituted $C_5$–$C_8$ cycloalkenyl, wherein the substituents are selected from the group consisting of hydrogen, $C_1$–$C_6$ alkyl, $NO_2$, halo, halo($C_1$–$C_6$)alkyl, $C_2$–$C_6$ alkenyl, $COR_5$, ($C_1$–$C_6$ alkyl)$_m$ amino, —$SR_5$, and $OR_5$;
E) A is a group of formula III;
F) A is a group of formula IV wherein $R_6$ and $R_7$ are $C_1$–$C_6$ alkyl or halo, and $R_8$ is hydrogen, $C_1$–$C_5$ alkyl, halo, $C_5$–$C_8$ cycloalkyl, phenyl or substituted-phenyl;
G) $R_2$ is hydrogen;
H) $R_3$ is hydrogen;
I) $R_4$ is substituted $C_5$–$C_8$ cycloalkenyl; wherein the substituents are selected from the group consisting of hydrogen, $NO_2$, halo, ($C_1$–$C_6$ alkyl)$_m$ amino, and $OR_5$;
J) A is a group of formula IV wherein $R_6$ is hydrogen, $R_7$ and $R_8$ are independently selected from the group consisting of halo and $C_1$–$C_4$ alkyl.
K) Q is $(CHR_2)R_4$;
L) $R^{30}$ and $R^{31}$ join to form a 3 to 6 member carbon ring;
M) $R^{30}$ and $R^{31}$ join to form a 3 to 5 member carbon ring;
N) $R^{30}$ and $R^{31}$ are each methyl;
O) $R_4$ is naphthyl;
P) $R_4$ is an optionally substituted bicyclic hydrocarbon ring system having 7 to 12 carbon atoms and 0, 1, 2, or 5 double bonds;
Q) $R_4$ is a 6 to 10 carbon atom unsaturated bicyclic ring system;
R) Q is bicyclic or substituted bicyclic;

S) $R_{34}$ is

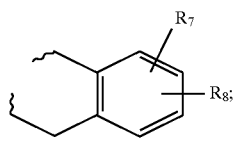

T) $R_{34}$ is an optionally substituted bicyclic ring substituent;
U) $R_9$ and $R_{10}$ are each hydrogen;
V) $R_9$ is selected from the group consisting of $C_1$–$C_6$ alkyl, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl-($C_1$–$C_3$)alkyl, $C_7$–$C_{16}$ arylalkyl;
W) $R_4$ is aromatic;
X) $R_{34}$ is spiro-bicyclic or substituted spiro-bicyclic;
Y) Q is hydrogen.

The more preferred classes have the following features:
A-C, E or F, I, L, N, P, R, and W.
The most preferred class of compounds has the following features:
A, G-J, M, and Q.
The preferred classes of compounds for use as selective 5-HT$_{2B}$ ligands have the following features:
A-D, E or J, M, and O.
The most preferred class of compounds for use as selective 5-HT$_{2B}$ ligands has the following features:
A, G-J, M, and O.

Compounds of Formulas I and II are particularly useful for modulating 5HT$_{2B}$ receptors. Certain compounds within the scope of this invention are preferred for that use. The following invention embodiments and compound characteristics listed in tabular form may be independently selected or combined to produce a variety of preferred compounds and embodiments of the invention. The following list of embodiments of this invention is in no way intended to limit the scope of this invention in any way.

A) $R_9$ and $R_{10}$ are each hydrogen;
B) $R_{11}$ is $C_1$–$C_3$ alkyl;
C) $R_{11}$ is chloro, fluoro, or bromo;
D) $R_{11}$ is —$OCH_3$;
E) $R^{30}$ and $R^{31}$ join to form a 3 to 8 member carbon ring;
F) $R^{30}$ and $R^{31}$ join to form a 3 to 6 member carbon ring;
G) A compound having preferred compound characteristics described supra;
H) A method for binding a 5HT$_{2B}$ receptor using one or more compounds of Formula I and/or II;
I) A method of using one or more compounds of Formula I and/or II for treating a functional bowel disorder.
I) A method of using one or more compounds of Formula I and/or II which are useful for modulation of the 5HT$_{2B}$ receptor for treating a function bowel disorder.
J) A method for using one or more compounds of Formula I and/or II for treating Irritable Bowel Syndrome.
K) A pharmaceutical formulation comprising a compound of Formula I and/or II and one or more pharmaceutically acceptable excipients.

Examples of compounds of Formula I include but are not limited to:
10-methyl-2,3,4,4a,5,6,7,11c-octahydro-1H-indolo[2,3-c] quinoline, 8-chloro-2,3,4,4a,5,6,7,11c-octahydro-1H-indolo[2,3-c]quinoline, 6-(2,4-dimethoxybenzyl)-10- methyl-2,3,4,4a,5,6,7,11c-octahydro-1H-indolo[2,3-c] quinoline, 7-fluoro-6-(2,4-dimethoxybenzyl)-10-methyl-2,3,4,4a,5,6,7,11c-octahydro-1H-indolo[2,3-c]quinoline, 8-methoxy-6-(2,4-dimethoxybenzyl)-10-methyl-2,3,4,4a, 5,6,7,11c-octahydro-1H-indolo[2,3-c]quinoline, 7-nitro-6-(3,4-dimethoxybenzyl)-10-methyl-2,3,4,4a,5,6,7,11c-octahydro-1H-indolo[2,3-c]quinoline, 5-(2,4-dimethoxybenzyl)-10-methyl-2,3,4,4a,5,6,7,11c-octahydro-1H-indolo[2,3-c]quinoline, 7-bromo-5-(2,4-dimethoxybenzyl)-10-methyl-2,3,4,4a,5,6,7,11c-octahydro-1H-indolo[2,3-c]quinoline, 6-ethoxy-5-(3,4-dimethoxybenzyl)-10-methyl-2,3,4,4a,5,6,7,11c-octahydro-1H-indolo[2,3-c]quinoline, 7-nitro-6-(3,4-dimethoxybenzyl)-10-methyl-2,3,4,4a,5,6,7,10c-octahydro-1H-indolo[2,3-c]quinoline, 7-(3,4-dimethoxybenzyl)-10-methyl-2,3,4,4a,5,6,7,11c-octahydro-1H-indolo[2,3-c]quinoline, 7-nitro-6-(3,4-diethoxybenzyl)-10-methyl-2,3,4,4a,5,6,7,11c-octahydro-1H-indolo[2,3-c]quinoline, 6-methyl-8-bromo-1-[(3,4-dimethoxyphenyl)-10-methyl-2,3,4,4a,5, 6,7,11c-octahydro-1H-indolo[2,3-c]quinoline, 7-(1,1-dimethylethyl)-5-(1-naphthalenyl-1-ethyl)-1,2,3,4,4a,5,6, 10c-pyrido[3,4-b]indole hydrochloride, 7-methyloxy-1-(2-methylaminonaphthalenyl)-1-ethyl)-1,2,3,4,4a,5,6, 10c-octahydrocyclopenta[a]pyrido[3,4-b]indole, (Z) 2-butenedioate, 6-(1,1-dimethylethyl)-1-(1-(3-diethylaminonaphthalenyl)-1-ethyl)-1,2,3,4,4a,5,6,10c-octahydrocyclopenta[a]pyrido[3,4-b]indole hydrochloride, and 6-methyl-5-[(4-dimethylaminonaphthalenyl)methyl]-1,2,3,4,4a,5,6,10c-octahydrocyclopenta[a]pyrido[3,4-b]indole dihydrochloride.

Examples of compounds of Formula II include but are not limited to:

3-(2-amino-cyclopentyl)-6,7-dimethylindole, 3-(2-amino-cyclopentyl)-5-methyl-7-bromoindole, 3-(2-amino-cyclopentyl)-6-methyl-7-chloroindole, 3-(2-amino-cyclopentyl)-6-bromo-7-methylindole, 3-(2-amino-cyclopentyl)-benz(G)indole, 3-(2-amino-cyclohexyl)-5-methyl-7-chloroindole, 3-(2-amino-cyclohexyl)-7-chloroindole, 3-(2-amino-cyclopropyl)-7-methoxyindole, 3-(2-amino-cycloheptyl)-7-fluoroindole, 3-(2-amino-cyclohexyl)-7-bromoindole, 3-(2-amino-cyclopropyl)-6-methyl-7-bromoindole, 3-(2-amino-cyclopentyl)-5-fluoro-7-methoxyindole, 3-(2-amino-cyclopentyl)-5-nitro-7-chloroindole, 3-(2-amino-cyclooctyl)-2-ethyl-7-fluoroindole, and 3-(2-amino-cycloheptyl)-2-methyl-7-fluoroindole.

The present invention contemplates racemic mixtures as well as the substantially pure stereoisomers of the compounds of Formulas I and II. The term "enantiomer" is used herein as commonly used in organic chemistry to denote a compound which rotates the plane of polarization. Thus, the "− enantiomer" rotates the plane of polarized light to the left, and contemplates the levorotary compound of Formulas I and V. The + and − enantiomers can be isolated using well-known classical resolution techniques. One particularly useful reference which describes such methods is JACQUES et. al. ENANTIOMERS, RACEMATES, AND RESOLUTIONS (John Wiley and Sons 1981). Appropriate resolution methods include direct crystallization, entrainment, and crystallization by optically active solvents. Chrisey, L. A. Heterocycles, 267:30 (1990). A preferred resolution method is crystallization with an optically active acid or by chiral synthesis as described in Example 46 using the method of A. I. Meyers. Loewe, M. F. et al., Tetrahedron Letters, 3291:26 (1985), Meyers, A. I. et al., J. Am. Chem. Soc., 4778:110 (1988). Preferred optically active acids include camphorsulfonic and derivatives of tartaric acid.

The present invention encompasses both the R and the S configurations. The terms "R" and "S" are used herein as commonly used in organic chemistry to denote the specific configuration of a chiral center. See, R. T. Morrison and R. N. Boyd, Organic Chemistry, pp 138–139 (4th Ed. Allyn & Bacon, Inc., Boston) and Orchin, et al. The Vocabulary of Organic Chemistry, p. 126, (John Wiley and Sons, Inc.). Thus the present invention encompasses both the cis and trans conformation of each particular compound.

The compounds of the present invention are known to form hydrates and solvates with appropriate solvents. Preferred solvents for the preparation of solvate forms include water, alcohols, tetrahydrofuran, DMF, and DMSO. Preferred alcohols are methanol and ethanol. Other appropriate solvents may be selected based on the size of the solvent molecule. Small solvent molecules are preferred to facilitate the corresponding solvate formation. The solvate or hydrate is typically formed in the course of recrystallization or in the course of salt formation. One useful reference concerning solvates is Sykes, Peter, A Guidebook to Mechanism in Organic Chemistry, 6:56 (1986, John Wiley & Sons, New York). The term "solvate" as used herein includes hydrate forms such as monohydrate and dihydrates.

The compounds of the present invention can be prepared using chemical processes that are understood in the art; however, a most preferred method for preparing the compounds of Formulas I and II is illustrated by Scheme I

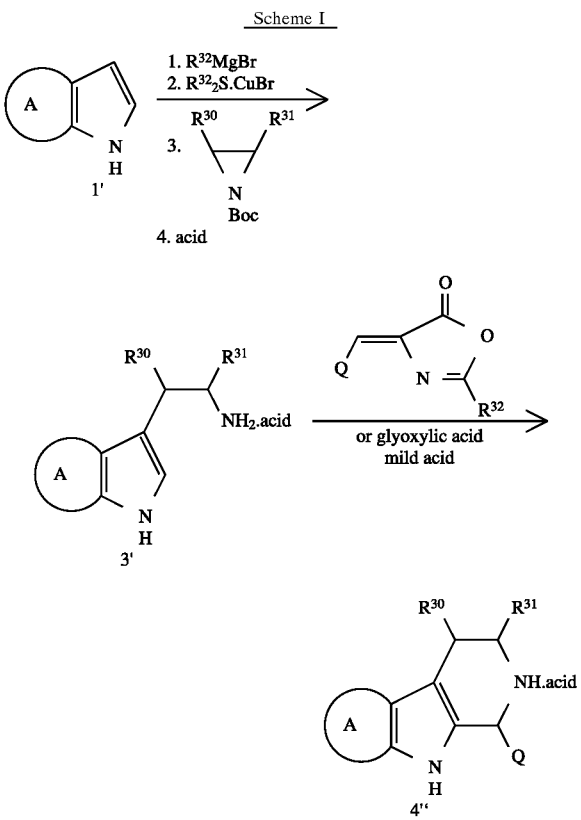

Scheme I wherein $R^{32}$ is independently selected from $C_1$–$C_6$ alkyl; $R^{30}$, $R^{31}$, A, and Q are defined supra.

Further, compounds of Example 19 can be prepared as illustrated by the following Scheme II:

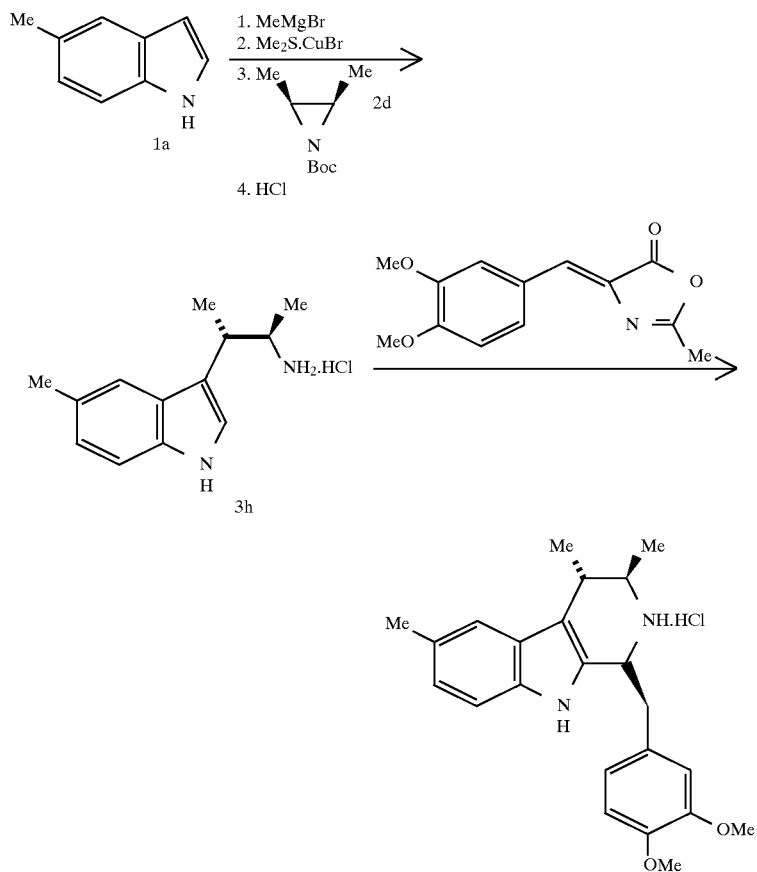
compounds of Example 20 can be prepared as illustrated by the following Scheme III:
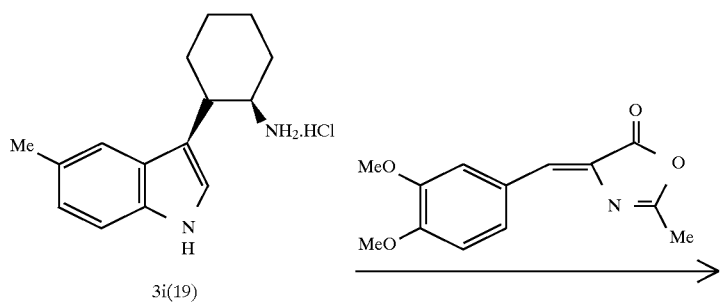

-continued
Scheme III

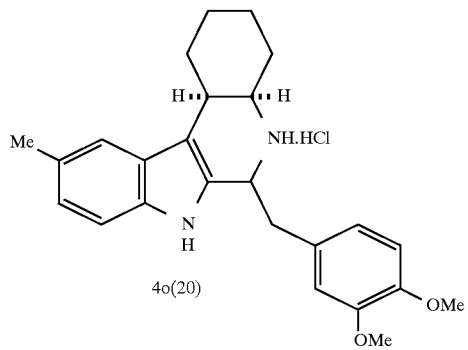

4o(20)

The following Examples further illustrate the preparation of certain of the Formula I and II compounds. The examples are illustrative only, and are not intended to limit the scope of the invention.

The column chromatography procedures used standard flash chromotagraphy techniques. One well-known reference describing appropriate flash chromatography techniques is Still, W. C. Kahn, and Mitra, *J. Org. Chem.*, 43, 2932, (1978). Fractions containing product were generally evaporated under reduced vacuum to provide the product.

Optical rotations were obtained using methanol, pyridine, or other suitable solvent.

The hydrochloride salt of the particular compound was prepared by placing the free base into diethyl ether containing an alcohol such as methanol or other suitable solvent mixture. While stirring this ether solution, a solution of HCl in diethyl ether was added dropwise until the solution became acidic. Alternatively, the ether solution was treated with dry HCl gas.

The maleate salt of the particular compound was prepared by placing the free base in ethyl acetate or other suitable solvent and treating with maleic acid. The precipitate formed was filtered and dried to provide the corresponding hydrochloride or maleate salt of the free base.

For Examples 1 through 20, where applicable, diethyl-ether was distilled from sodium benzophenone ketyl prior to use. All reactions were performed under a positive pressure of argon. $^1$H-NMR and $^{13}$C-NMR data were recorded on a Bruker AC-200P (200 MHz). IR spectra were obtained on Nicolet 510 P-FT (film and KBr). Melting points were determined on a Büchi apparatus and are not corrected. Analytical TLC was performed on Merck TLC glass plates precoated with $F_{254}$ silica gel 60 (UV, 254 nm and Iodine). Chromatographic separations were performed by using 230–400 mesh silica gel (Merck). N-BOC-aziridines (2a–d) were prepared from the corresponding alkenes following standard procedures.

Preparation 1

Indole starting materials

The indole starting materials (1a, 1b, and 1c) infra. were purchased (1a), prepared according to Bartoli's procedure (1b) [Bartoli, G. et al. *Tetrahedron Lett.,* 1989, 30, 2129] or (1c) synthesized from 2-iodo-4,6-dimethylaniline (5'''). The process is illustrated by the following Scheme IV:

Scheme IV

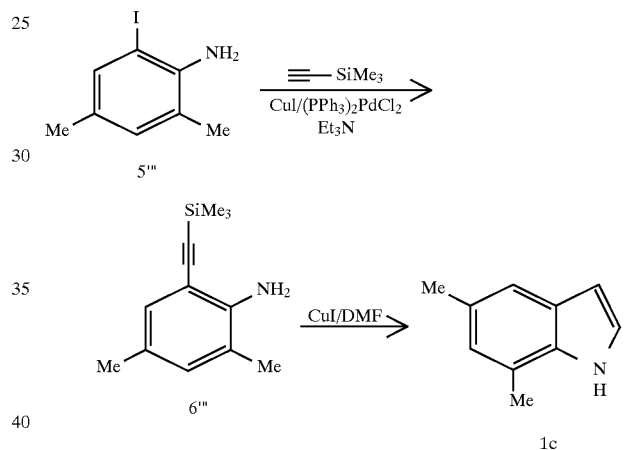

The 2-Iodo-4,6-dimethylaniline (5''') synthesis can be completed as follows: To a suspension of 5''' (24 mmol.), CuI (0.05 equiv.) and $(PPh_3)_2PdCl_2$ (0.05 equiv.) in 30 ml of dry triethylamine under Ar atmosphere was added trimethylsilylacetylene (1.1 equiv.) and the resulting mixture was stirred for 3 hours. Then, the solvent was eliminated under vacuum and the residue purified by flash chromatography using hexane/ethyl acetate (3:1) as eluent to yield 6' in quantitative yield. A slurry of 6''' (23 mmol.) and CuI (2 equiv.) in 50 ml of dry dimethylformamide was heated for 2.5 h. under Ar atmosphere at 100° C. After cooling down to room temperature the reaction mixture was filtered off and the solid washed twice with ether (20 ml.). The organic phase was washed with water (3×50 ml.), dried over $Na_2SO_4$ and the solvent evaporated to dryness. The crude product was purified by flash chromatography using hexane/ethyl acetate (3:1) as eluent to afford 1c (1.5 g., 45%).

The process for preparing compounds of Examples 1 through 18 is illustrated by the following Scheme:

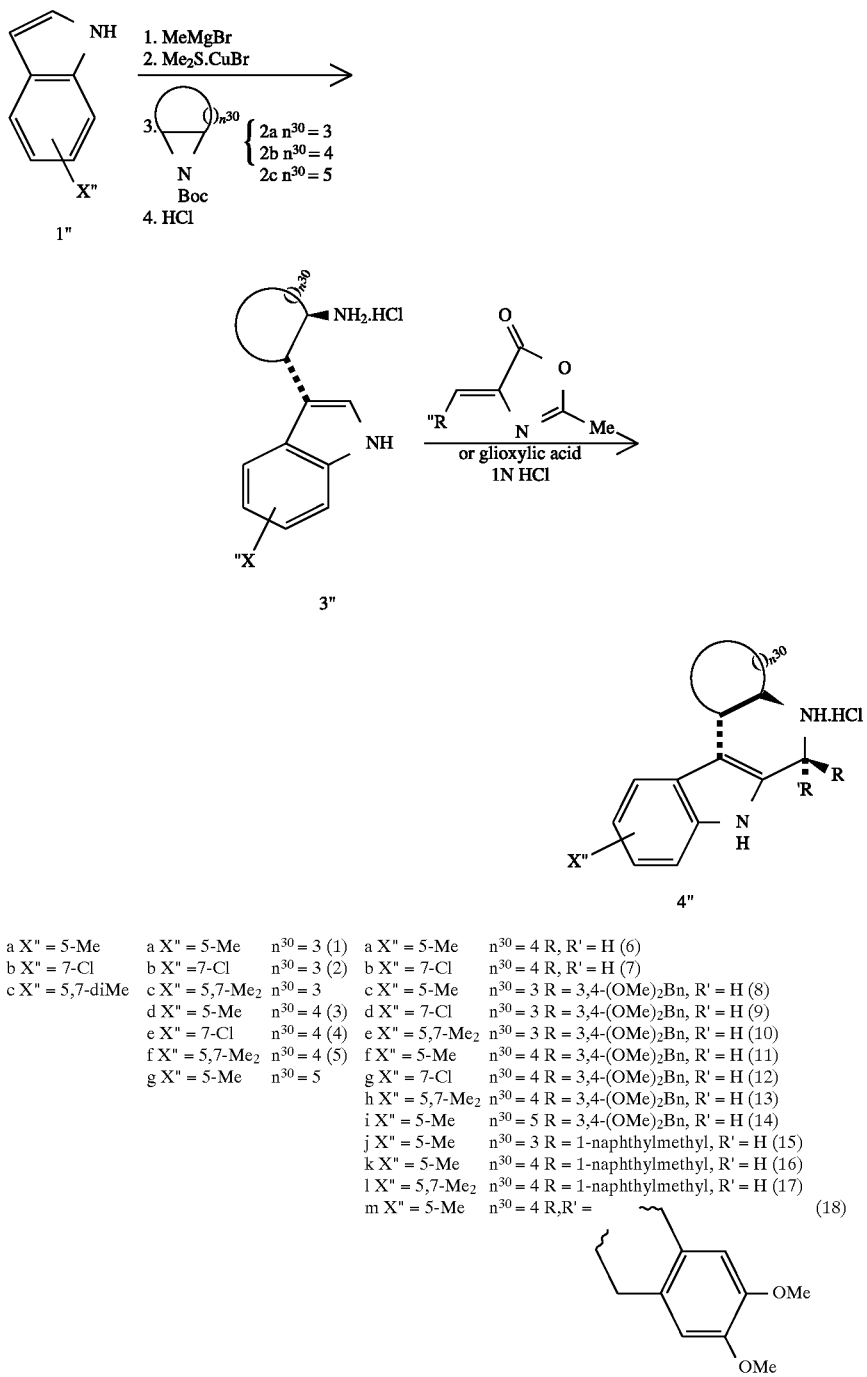

| | | | | |
|---|---|---|---|---|
| a X" = 5-Me | a X" = 5-Me | $n^{30} = 3$ (1) | a X" = 5-Me | $n^{30} = 4$ R, R' = H (6) |
| b X" = 7-Cl | b X" = 7-Cl | $n^{30} = 3$ (2) | b X" = 7-Cl | $n^{30} = 4$ R, R' = H (7) |
| c X" = 5,7-diMe | c X" = 5,7-Me$_2$ | $n^{30} = 3$ | c X" = 5-Me | $n^{30} = 3$ R = 3,4-(OMe)$_2$Bn, R' = H (8) |
| | d X" = 5-Me | $n^{30} = 4$ (3) | d X" = 7-Cl | $n^{30} = 3$ R = 3,4-(OMe)$_2$Bn, R' = H (9) |
| | e X" = 7-Cl | $n^{30} = 4$ (4) | e X" = 5,7-Me$_2$ | $n^{30} = 3$ R = 3,4-(OMe)$_2$Bn, R' = H (10) |
| | f X" = 5,7-Me$_2$ | $n^{30} = 4$ (5) | f X" = 5-Me | $n^{30} = 4$ R = 3,4-(OMe)$_2$Bn, R' = H (11) |
| | g X" = 5-Me | $n^{30} = 5$ | g X" = 7-Cl | $n^{30} = 4$ R = 3,4-(OMe)$_2$Bn, R' = H (12) |
| | | | h X" = 5,7-Me$_2$ | $n^{30} = 4$ R = 3,4-(OMe)$_2$Bn, R' = H (13) |
| | | | i X" = 5-Me | $n^{30} = 5$ R = 3,4-(OMe)$_2$Bn, R' = H (14) |
| | | | j X" = 5-Me | $n^{30} = 3$ R = 1-naphthylmethyl, R' = H (15) |
| | | | k X" = 5-Me | $n^{30} = 4$ R = 1-naphthylmethyl, R' = H (16) |
| | | | l X" = 5,7-Me$_2$ | $n^{30} = 4$ R = 1-naphthylmethyl, R' = H (17) |
| | | | m X" = 5-Me | $n^{30} = 4$ R,R' = (18) |

EXAMPLE 1

Trans-3-(2-amino-cyclopentyl)-5-methylindole, hydrochloride

To a suspension of the corresponding indole 1a (5 mmol.) in 10 ml of anhydrous ether under Ar atmosphere was added a 3M solution of methylmagnesium bromide (1.5 equiv.). The resulting mixture was stirred for 45 min. at room temperature. Then, this mixture was cannulated to a slurry of Copper (I) bromide-dimethylsulfide complex (0.2 equiv.) in 5 ml. of dry ether under Ar atmosphere at −30° C. The reaction mixture was stirred for 30 min. at the same temperature. After this time the mixture was cooled down to −78° C. and the corresponding aziridine 2a (1.5 equiv.) dissolved in 10 ml. of dry ether was added. The whole mixture was allowed to reach room temperature and stirring was kept overnight. The reaction was quenched with 10 ml. of a saturated solution of ammonium chloride. The layers were separated and the aqueous phase was extracted with ether/ethyl acetate (1:1) (2×10 ml.). The combined organic extracs were dried over anhydrous sodium sulfate, the solvent was eliminated under vacuum and the residue was purified by flash chromatography using hexane/ethyl acetate (3:1). The corresponding N-BOC protected tryptamine was dissolved in dichloromethane/ether. The solution was saturated with dry hydrogen chloride and stirred overnight at room temperature. Finally, the solvent was evaporated and the crude title tryptamines purified by washing with dichoromethane/ether/methanol mixture (2:3:1). The product was identified as the title compound (3a).

Yield: 85%. Mp: >200° C. $^1$H NMR (CD$_3$OD), δ: 7.35 (s,1H), 7.23–7.12 (m, 2H), 6.91 (d, J=7.5 Hz, 1H), 3.73 (m, 1H), 3.27 (m, 1H), 2.38–2.10 (m, 5H), 2.05–1.70 (m, 4H). $^{13}$C NMR (CD$_3$OD), δ: 136.98, 128.93, 127.84, 124.27, 123.13, 119.01, 114.19, 112.37, 58.56, 43.93, 33.10, 31.30, 23.07, 21.73. IR (KBr): 3304, 2963, 1593, 1510, 1481, 800 cm$^{-1}$. MS (EI): 214 (M$^+$-HCl, 28), 197 (70), 170 (14), 144 (42), 126 (49), 105 (33), 84 (100).

EXAMPLE 2

Trans-3-(2-amino-cyclopentyl)-7-chloroindole, hydrochloride

The title compound (3b) was prepared using substantially the same procedure as described by Example 1; however, the indole starting material was a compound of Formula 1b.

Yield: 37%. Mp: >200° C. $^1$H NMR (CD$_3$OD), δ: 7,56 (d, J=7.7 Hz, 1H), 7.31 (s, 1H), 7.12 (d J=7.3 Hz, 1H), 7.01 (t, J=7.8 Hz, 1H), 3.77 (q, J=7.9 Hz, 1H), 3.40–3.25 (m, 1H), 2.40–2.15 (m, 2H), 2.05–1.70 (m, 4H). $^{13}$C NMR (CD$_3$OD), δ: 135.48, 129.53, 124.28, 122.13, 120.79, 118.40, 118.02, 116.18, 58.55, 43.79, 33.32, 31.36, 23.11. IR (KBr): 3422, 3298, 3040, 2972, 2909, 1495 cm$^{-1}$. MS (EI): 235 (M$^+$-Cl, 100), 218 (28), 165 (7).

EXAMPLE 3

Trans-3-(2-amino-cyclohexyl)-5-methylindole, hydrochloride

The title compound (3d) was prepared using substantially the same procedure as described by Example 1.

Yield: 80%. Mp: >200° C. $^1$H NMR (CD$_3$OD), δ: 7,44 (s, 1H), 7.27 (d, J=8.3 Hz, 1H), 7.18 (s, 1H), 6.95 (dd, J=8.3 and 1.2 Hz, 1H), 3.55–3.40 (m, 1H), 2.86 (dt, J=4.3 and 11.3 Hz, 1H), 2.42 (s, 3H), 2.25–2.12 (m, 1H), 2.10–1.79 (m, 4H), 1.75–1.40 (m, 3H). $^{13}$C NMR (CD$_3$OD), δ: 136.97, 129.12, 127.74, 124.42, 123.73, 119.09, 114.77, 112.48, 56.22, 41.61, 34.75, 32.42, 26.93, 25.79, 21.73. IR (KBr): 3400, 3283, 3021, 2936, 2861, 1491 cm$^{-1}$. MS (EI): 229 (M$^+$-Cl, 100).

EXAMPLE 4

Trans-3-(2-amino-cyclohexyl)-7-chloroindole, hydrochloride (3e)

The title compound (3e) was prepared using substantially the same procedure as described by Example 1.

Yield: 43%. Mp: >200° C. $^1$H NMR (CD$_3$OD), δ: 7,63 (d, J=7.8 Hz, 1H), 7.35 (s, 1H), 7.14 (d, J=7.4 Hz, 1H), 7.02 (t, J=7.7 Hz, 1H), 3.60–3.40 (s, 1H), 3.08–2.91 (m, 1H), 2.30–2.10 (m, 1H), 2.05–1.80 (m, 4H), 1.75–1.45 (m, 3H). $^{13}$C NMR (CD$_3$OD), δ: 135.43, 129.41 125.00, 122.15, 120.87, 118.53, 118.09, 116.70, 56.12, 41.43, 34.74, 32.37, 26.80, 25.68. IR (KBr): 2938, 2859, 1429, 1341, 779, 735 cm $^{-1}$. MS (EI): 249 (M$^+$-Cl, 100).

EXAMPLE 5

Trans-3-(2-amino-cyclopentyl)-5,7-dimethylindole, hydrochloride

The title compound (3f) was prepared using substantially the procedure of Example 1; however, the indole was 1c and the aziridine was 2b.

Yield: 45%. Mp: >200° C. $^1$H NMR (CD$_3$OD), δ: 7,27 (s, 1H), 7.19 (s, 1H), 6.77 (s, 1H), 3.42 (dt, J=11.0 and 4.2 Hz, 1H), 2.85 (dt, J=11.4 and 4.2 Hz, 1H), 2.44 (s, 3H), 2.39 (s, 3H), 2.30–2.10 (m, 1H), 2.08–1.83 (m, 4H), 1.70–1.40 (m, 3H). $^{13}$C NMR (CD$_3$OD), δ: 136.39, 129.37, 127.39, 125.01, 123.56, 121.94, 116.78, 115.16, 56.28, 41.70, 34.71, 32.40, 26.93, 25.80, 21.72, 16.93. IR (KBr): 3420, 3279, 3013, 2934, 2861, 1505 cm$^{-1}$. MS (EI): 242 (M$^+$-HCl, 62), 225 (25), 199 (23), 184 (20), 171 (38), 158 (100), 145 (18), 128 (12), 115 (12), 97 (12).

Substantially the same procedure was used to prepare Trans-3-(2-amine-cyclopentyl)-5,7-dimethylindole, hydrochloride (3c); however, the aziridine was 2a.

Yield: 63%. $^1$H NMR (DMSO-d$_6$), δ: 10.8 (s, 1H), 8.12 (broad s, 3H), 7.30–7.20 (m, 2H), 6.70 (s, 1H), 3.70–3.55 (m, 1H), 3.55–3.20 (m, 1H), 2.38 (s, 3H), 2.36 (s, 3H), 2.30–2.10 (m, 2H), 2.00–1.60 (m, 4H).

EXAMPLE 6

Trans-10-methyl-2,3,4,4a,5,6,7,11c-octahydro-1H-indolo[2,3-c]quinoline, hydrochloride A suspension of tryptamine hydrochloride (3a) (1.3 mmol.) in 10 ml. of distilled water was dissolved by heating. To this solution glyoxylic acid (1.43 mmol.) in 1 ml. of water was added. Subsequently, a solution of KOH (1.3 mmol.) in 1 ml. of distilled water was slowly added to reach pH=4. The resulting solution was stirred at room temperature for 1 h. After this time, commercially available hydrochloric acid (0.5 ml.) was added dropwise and the resulting mixture was refluxed for 30 min. Another portion of hydrochloric acid (0.5 ml.) was added and the reaction further refluxed for 15 min. Finally, the reaction mixture was cooled down to room temperature and filtered off. The title tetrahydro-b-carboline (4a) was subsequently washed with water and ethanol.

Yield: 81%. Mp: >200° C. $^1$H NMR (DMSO-d$_6$), δ: >11.0 (s, 1H), 9.92 (broad s, 1H), 9.68 (broad s, 1H), 7.38 (s, 1H), 7.23 (d, J=8.3 Hz, 1H), 6.88 (d, J=7.8 Hz, 1H), 4.50–4.22 (m, 2H), 3.18–2.95 (m, 2H), 2.80–2.65 (m, 1H), 2.34 (s, 3H), 2.30–2.15 (m, 1H), 1.98–1.80 (m, 2H), 1.80–1.20 (4H). $^{13}$C NMR (DMSO-d$_6$), δ: 134.75 127.31, 126.49, 125.64, 122.65, 119.11, 111.14, 108.82, 58.99, 37.18, 29.42, 28.84, 24.94, 24.43, 21.28. IR (KBr): 3391, 3266, 2936, 2861, 2801, 2762 cm$^{-1}$. MS (EI): 241 (M$^+$-Cl, 100).

EXAMPLE 7

Trans-8-chloro-2,3,4,4a,5,6,7,11c-octahydro-1H-indolo[2,3-c]quinoline, hydrochloride (4b)

A suspension of tryptamine hydrochloride (3b) (1.3 mmol.) in 10 ml. of distilled water was dissolved by heating. To this solution glyoxylic acid (1.43 mmol.) in 1 ml. of water was added. Subsequently, a solution of KOH (1.3 mmol.) in 1 ml. of distilled water was slowly added to reach pH=4. The resulting solution was stirred at room temperature for 1 h. After this time, commercially available hydrochloric acid (0.5 ml.) was added dropwise and the resulting mixture was refluxed for 30 min. Another portion of hydrochloric acid (0.5 ml.) was added and the reaction further refluxed for 15 min. Finally, the reaction mixture was cooled down to room temperature and filtered off. The title tetrahydro-b-carboline (4b) was subsequently washed with water and ethanol.

Yield: 45%. Mp: >200° C. $^1$H NMR (DMSO-d$_6$), δ: >11.0 (s, 1H), 10.05 (broad s, 1H), 9.87 (broad s, 1H), 7.58 (d, J=7.8 Hz, 1H), 7.16 (d, J=7.6 Hz, 1H), 6.98 (t, J=7.9 Hz, 1H), 4.60–4.20 (m, 2H), 3.18–2.95 (m, 2H), 2.90–2.70 (m, 1H), 2.25–2.18 (m, 1H), 1.98–1.75 (m, 2H), 1.65–1.20 (4H). $^{13}$C NMR (DMSO-d$_6$), δ: 133.17 128.18, 127.23, 120.65, 120.03, 118.55, 115.78, 110.73, 58.74, 36.93, 29.16, 28.77, 24.88, 24.36. IR (KBr): 3422, 3231, 2936, 2861, 2760, 1429 cm$^{-1}$. MS (EI): 261 (M$^+$-Cl, 30), 241 (100).

EXAMPLE 8

Trans-5-(3,4-dimethoxybenzyl)-9-methyl-1,2,3,4,4a, 5,6,10c-octahydrocyclopenta[a]pyrido[3,4-b]indole, hydrochloride (4c)

A suspension of the corresponding tryptamine hydrochloride (3a) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 88%. Mp: 187°–191° C. $^1$H NMR (DMSO-d$_6$), δ: >11.0 (s, 1H), 10.38 (broad s, 1H), 9.25 (broad s, 1H), 7.50–7.15 (m, 3H), 7.15–6.80 (m, 3H), 5.0–4.70 (broad s, 1H), 3.75 (s, 6H), 3.40–2.80 (m), 2.49 (s, 3H), 2.20–1.70 (m, 4H), 1.55–1.30 (broad s, 1H). $^{13}$C NMR (DMSO-d$_6$), δ: 148.73 147.90, 134.45, 130.24, 128.17, 127.64, 125.44, 123.03, 121.78, 118.43, 113.69, 111.95, 111.27, 110.64, 62.01, 57.50, 55.51, 37.49, 25.52, 25.14, 21.30, 20.73. IR (KBr): 3438, 3237, 2942, 1518, 1264, 1248 cm$^{-1}$. MS (EI): 377 (M$^+$-Cl, 100).

EXAMPLE 9

Trans-7-chloro-5-(3,4-dimethoxybenzyl)-1,2,3,4,4a, 5,6,10c-octahydrocyclopenta[a]pyrido[3,4-b]indole, hydrochloride (4d)

A suspension of the corresponding tryptamine hydrochloride (3b) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 52%. Mp: >230° C. dec. $^1$H NMR (DMSO-d$_6$), δ: >11.0 (s, 1H), 10.40 (broad s, 1H), 9.30 (broad s, 1H), 7.60–7.42 (m, 1H), 7.38–6.90 (m, 5H), 4.90–4.75 (broad s, 1H), 3.78 (s, 3H), 3.76 (s, 3H), 3.40–3.00 (m), 2.15–1.80 (m, 4H), 1.60–1.35 (broad s, 1H). $^{13}$C NMR (DMSO-d$_6$), δ: 148.70, 147.91, 132.95, 131.78, 128.25, 127.02, 121.75, 121.11, 120.41, 117.96, 116.05, 113.54, 112.72, 111.99, 61.74, 57.45, 55.50, 37.27, 25.24, 25.07, 20.77. IR (KBr): 3588, 3438, 1518, 1290 cm$^{-1}$. MS (EI): 398 (M$^+$+2-HCl, 40), 396 (M$^+$-HCl, 100).

EXAMPLE 10

Trans-5-(3,4-dimethoxybenzyl)-7,9-dimethyl-1,2,3, 4,4a,5,6,10c-octahydrocyclopenta[a]pyrido[3,4-b]indole, hydrochloride (4e)

A suspension of the corresponding tryptamine hydrochloride (3c) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 87%. Mp: >200° C. $^1$H NMR (DMSO-d$_6$), δ: >11.0 (s, 1H), 10.20 (broad s, 1H), 9.20 (broad s, 1H), 7.29 (s, 1H), 7.20–6.95 (m, 3H), 6.75 (s, 1H), 4.90–4.70 (broad s, 1H), 3.78 (s, 6H), 3.30–2.90 (m), 2.48 (s, 3H), 2.34 (s, 3H), 2.10–1.70 (m, 4H), 1.60–1.30 (broad s, 1H). $^{13}$C NMR (DMSO-d$_6$), δ: 148.73, 147.90, 134.01, 129.98, 128.31, 127.84, 125.10, 123.82, 121.75, 120.42, 116.03, 113.58, 111.99, 111.21, 61.94, 57.62, 55.52, 37.60, 25.57, 25.17, 21.23, 20.75, 17.07. IR (KBr): 3447, 2910, 1520 cm$^{-1}$. MS (EI): 391 (M$^+$-Cl, 100), 239 (35).

EXAMPLE 11

Trans-6-(3,4-dimethoxybenzyl)-10-methyl-2,3,4,4a, 5,6,7,11c-octahydro-1H-indolo[2,3-c]quinoline, hydrochloride (4f)

A suspension of the corresponding tryptamine hydrochloride (3d) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 85%. Mp: 197°–200° C. $^1$H NMR (DMSO-d$_6$), δ: >11.0(s, 1H), 8.90 (broad s, 1H), 7.42 (s, 1H), 7.28 (d, J=8.3 Hz, 1H), 7.16 (s, 1H), 7.05–6.90 (m, 3H), 4.95–4.80 (broad s, 1H), 3.73 (s, 6H), 3.66–3.59 (m, 1H), 3.25–2.80 (m, 4), 2.35 (s, 3H), 2.20–2.10 (m, 1H), 1.95–1.20 (m, 6H). $^{13}$C NMR (DMSO-d$_6$), δ: 148.67, 147.91, 134.92, 134.76, 129.72, 127.85, 127.45, 125.43, 122.91, 121.85, 119.43, 113.59, 111.90, 111.30, 109.45, 59.98, 55.47, 55.40, 37.08, 36.65, 29.48, 28.24, 24.94, 24.41, 21.32. IR (KBr): 3439, 2936, 1516, 1464, 1453, 1265 cm$^{-1}$. MS (EI): 391 (M$^+$-Cl, 100).

EXAMPLE 12

Trans-8-chloro-6-(3,4-dimethoxybenzyl)-2,3,4,4a,5, 6,7,11c-octahydro-1H-indolo[2,3-c]quinoline, hydrochloride (4g)

A suspension of the corresponding tryptamine hydrochloride (3e) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 47%. Mp: >250° C. $^1$H NMR (DMSO-d$_6$), δ: >11.0 (s, 1H), 9.75 (broad s, 1H), 8.90 (broad s, 1H), 7.64 (d, J=7.9 Hz, 1H), 7.20 (d, J=7.8 Hz 1H), 7.15–7.00 (m, 4H), 4.90–4.80 (broad s, 1H), 3.74 (s, 6H), 3.70–3.60 (m, 1H), 3.25–2.85 (m, 4H), 2.20–2.15 (m, 1H), 1.95–1.25 (m, 6H). $^{13}$C NMR (DMSO-d$_6$), δ: 148.72, 148.00, 133.46, 131.35, 128.00, 127.08, 121.86, 121.13, 120.28, 119.01, 115.99, 113.41, 111.98, 111.66, 59.62, 55.53, 55.42, 54.98, 37.24, 36.49, 29.23, 28.25, 24.88, 24.34. IR (KBr): 3428, 2938, 1518, 1250 cm$^{-1}$. MS (EI): 410 (M$^+$-HCl, 100).

EXAMPLE 13

Trans-6-(3,4-dimethoxybenzyl)-8,10-dimethyl-2,3,4, 4a,5,6,7,11c-octahydro-1H-indolo[2,3-c]quinoline, hydrochloride (4h)

A suspension of the corresponding tryptamine hydrochloride (3f) (1 mmol) and the correponding 4-alkylidene-2- methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 78%. Mp: 198°–202° C. $^1$H NMR (DMSO-d$_6$), δ: 10.88 (s, 1H), 9.81 (broad s, 1H), 8.78 (broad s, 1H), 7.24 (s, 1H), 7.20 (s, 1H), 7.10–6.90 (m, 2H), 6.73 (s, 1H), 4.90–4.75 (broad s, 1H), 3.74 (s, 6H), 3.25–3.10 (m, 2H), 3.10–2.80 (m, 2H), 2.45 (s, 3H), 2.32 (s, 3H), 2.20–2.10 (m, 1H), 2.00–1.80 (m, 3H), 1.60–1.10 (m, 3H), $^{13}$C NMR (DMSO-d$_6$), δ: 148.65 147.87, 134.44, 129.55, 128.17, 127.59, 125.13, 123.68, 121.90, 120.36, 117.05, 113.64, 111.89, 110.04, 59.89, 55.78, 55.41, 37.17, 36.56, 29.47, 28.21, 24.94, 24.43, 21.26, 17.09. IR (KBr): 3450, 2936, 1516, 1493, 1264, 1240 cm$^{-1}$. MS (EI): 405 (M$^+$-Cl, 100).

EXAMPLE 14

Trans-7-(3,4-dimethoxybenzyl)-11-methyl-1,2,3,4,5,5a,6,7,8,12a-decahydrocyclohepta[a]pyrido[3,4-b]indole, hydrochloride (4i)

A suspension of the corresponding tryptamine hydrochloride (3g) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 35%. Mp: 187°14 190° C. $^1$H NMR (DMSO-d$_6$), δ: >11.0 (s, 1H), 9.66 (broad s, 1H), 7.29–7.25 (m, 2H), 6.92 (d, J=7.8 Hz, 1H), 6.81 (d, J=8.2 Hz, 1H), 6.65–6.56 (m, 2H) 4.80–4.70 (broad s, 1H), 3.66 (s, 3H), 3.43 (s, 3H), 3.00–2.90 (m, 1H), 2.90–2.70 (m, 1H), 2.35 (s, 3H), 2.35–2.20 (m, 1H), 1.80–1.30 (m, 8H), 0.85–0.65 (m, 1H). $^{13}$C NMR (DMSO-d$_6$), δ: 148.56 147.96, 135.12, 128.81, 128.05, 127.27, 125.32, 123.09, 121.73, 118.97, 113.32, 111.85, 111.31, 110.51, 55.60, 55.08, 54.97, 51.48, 36.97, 36.24, 32.74, 31.88, 26.37, 24.88, 24.14, 21.30. IR (KBr): 3414, 3343, 2932, 2859, 1516, 1265 cm$^{-1}$. MS (EI): 405 (M$^+$-Cl, 100), 335 (20).

EXAMPLE 15

Trans-9-methyl-5-(1-naphthylmethyl)-1,2,3,4,4a,5,6,10c-octahydrocyclopenta[a]pyrido [3,4-b]indole, hydrochloride (4j)

A suspension of the corresponding tryptamine hydrochloride (3a) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 78%. Mp: >200° C. $^1$H NMR (DMSO-d$_6$), δ: >11.0 (s, 1H), 10.45 (broad s, 1H), 9.03 (broad s, 1H), 8.46 (d, J=7.9 Hz, 1H), 8.12–7.90 (m, 3H), 7.70–7.40 (m, 3H), 7.40–7.25 (m, 2H), 6.96 (d, J=8.0 Hz, 1H), 5.15–4.90 (broad s, 1H), 4.45–4.30 (m, 1H), 3.65–3.50 (m), 3.15–2.95 (m, 1H), 2.38 (s, 3H), 2.00–1.70 (m, 4H), 1.60–1.35 (broad s, 1H). $^{13}$C NMR (DMSO-d$_6$), δ: 134.59, 133.86, 131.63, 131.32, 129.92, 129.18, 128.86, 128.07, 127.74, 126.38, 125.96, 125.83, 125.48, 124.08, 123.20, 118.52, 111.31, 110.97, 61.78, 55.76, 37.40, 35.13, 25.49, 25.12, 21.32, 20.67. IR (KBr): 3445, 3231, 2949, 2878, 2780, 793 cm$^{-1}$. MS (EI): 367 (M$^+$-Cl, 100).

EXAMPLE 16

Trans-10-methyl-6-(1-naphthylmethyl)-2,3,4,4a,5,6,7,11c-octahydro-1H-indolo[2,3-c]quinoline, hydrochloride (4k)

A suspension of the corresponding tryptamine hydrochloride (3d) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 80%. Mp: >200° C. $^1$H NMR (DMSO-d$_6$), δ: >11.0 (s, 1H), 8.40 (d, J=7.8 Hz, 1H), 8.01 (d, J=7.5 Hz, 1H), 7.92 (d, J=8.2 Hz, 1H), 7.74 (d, J=6.8 Hz, 1H), 7.70–7.40 (m, 4H), 7.35 (d, J=8.4 Hz, 1H), 6.97 (d, J=8.2 Hz, 1H), 5.15–4.90 (broad s, 1H), 4.50–4.30 (m, 1H), 3.50–3.10 (m, 2H), 3.10–2.82 (m, 2H), 2.38 (s, 3H), 2.10–1.20 (m, 7H). $^{13}$C NMR (DMSO-d$_6$), δ: 135.05, 134.90, 133.85, 131.79, 131.28, 129.36, 128.93, 128.07, 127.56, 126.33, 125.94, 125.83, 125.41, 124.02, 123.10, 119.54, 111.27, 109.61, 59.72, 53.97, 36.73, 35.27, 29.47, 28.37, 24.92, 24.36, 21.34. IR (KBr): 3447, 3235, 2936, 2857, 1450, 790 cm$^{-1}$. MS (EI): 381 (M$^+$-Cl, 100).

EXAMPLE 17

Trans-8,10-dimethyl-6-(1-naphthylmethyl)-2,3,4,4a,5,6,7,11c-octahydro-1H-indolo[2,3-c]quinoline, hydrochloride (4l)

A suspension of the corresponding tryptamine hydrochloride (3f) (1 mmol) and the correponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Yield: 77%. Mp: >200° C. $^1$H NMR (DMSO-d$_6$), δ: >11.0 (s, 1H), 10.11 (broad s, 1H), 8.52 (d, J=8.2 Hz, 1H), 8.35 (broad s, 1H), 8.02 (d, J=7.3 Hz, 1H), 7.92 (d, J=7.9 Hz, 1H), 7.82 (d, J=6.9 Hz, 1H), 7.71–7.46 (m, 3H), 7.29 (s, 1H), 6.78 (s, 1H), 5.10–4.90 (broad s, 1H), 4.70–4.50 (m, 1H), 3.40–3.20 (m, 2H), 3.10–2.80 (m, 2H), 2.51 (s, 3H), 2.34 (s, 3H), 2.05–1.90 (m, 1H), 1.80–1.70 (m, 2H), 1.60–1.20 (m, 4H). $^{13}$C NMR (DMSO-d$_6$), δ: 134.57, 133.87, 131.95, 131.42, 129.29, 129.11, 128.81, 128.04, 127.71, 126.21, 125.91, 125.83, 125.14, 124.46, 123.91, 120.46, 117.14, 110.25, 59.65, 54.03, 36.66, 35.25, 29.47, 28.32, 24.94, 24.35, 21.26, 17.30. IR (KBr): 3449, 2934, 2859, 2791, 1449, 779 cm$^{-1}$. MS (EI): 395 (M$^+$-Cl, 100).

EXAMPLE 18

Trans-spiro-6,6-[2-(3,4-dimethoxy)-1,2,3,4-tetrahydronaphthyl]-10-methyl-2,3,4,4a,5,6,7,11a-octahydro-1H-indolo[2,3-c]quinidine, hydrochloride (4m)

A suspension of the corresponding tryptamine hydrochloride (3a) (1 mmol) and the corresponding 4-alkylidene-2-methyloxazolin-5-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Epimeric mixture. Yield: 89%. $^1$H NMR (DMSO-d$_6$), δ: >11.0 (s, 1H), 10.12 (broad s, 1H), 8.72 (broad s, 1H), 7.42 (s, 1H), 7.21 (s, 1H), 6.90–6.60 (s, 3H), 3.75 (s, 3H), 3.71 (s, 3H), 3.30–2.80 (m, 5H), 2.35 (s, 3H), 2.00–1.20 (m, 6H). $^{13}$C NMR (DMSO-d$_6$), δ: 147.44, 134.84, 134.32, 133.98, 127.42, 126.53, 126.35, 125.25, 125.13, 123.60, 123.25, 122.98, 119.56, 119.43, 112.05, 111.48, 111.27, 108.78, 108.60, 57.83, 57.50, 56.07, 55.56, 36.40, 31.91, 30.74, 29.39, 29.21, 28.73, 28.41, 24.92, 24.38, 23.83, 21.30. IR (KBr): 3440, 2950, 1518, 1200, 1110, cm$^{-1}$. MS (EI): 417 (M$^+$-Cl, 100).

EXAMPLE 19

Trans-1-(3,4-dimethoxybenzyl)-3,4,6-trimethyl-1,2, 3,4,-tetrahydro-9-pyrido[3,4-b]indole, hydrochloride (4n)

Trans-3-(2-amine-1,2-dimethylethyl)-5-methylindole, hydrochloride (3h) was prepared using substantially the procedure of Example 1; however, the aziridine was 2c.

Yield: 71%. $^1$H NMR (CD$_3$OD), δ: 7,45 (s, 1H), 7.32 (d, J=8.3 Hz, 1H), 7.19 (s, 1H), 7.00 (dd, J=8.4 and 1.5 Hz, 1H), 3.66 (t, J=6.9 Hz, 1H), 3.28 (t, J=7.3 Hz, 1H), 2.47 (s, 3H), 1.48 (d, J=7.2 Hz, 3H), 1.38 (d, J=6.6 Hz, 3H). $^{13}$C NMR (CD$_3$OD), δ: 136.89, 129.19, 127.68, 124.46, 123.69, 119.09, 115.41, 112.44, 53.51, 36.62, 21.71, 17.06, 16.49.

Yield: 32%. Mp: 195°–199° C. $^1$H NMR (DMSO-d$_6$), δ: >11.0 (s, 1H), 9.40 (broad s, 1H), 8.90 (broad s, 1H), 7.40 (s, 1H), 7.30 (d, J=8.2 Hz, 1H), 7.08 (s, 1H), 6.96–6.90 (m, 3H), 4.90–4.80 (broad s, 1H), 3.73 (s, 3H), 3.72 (s, 3H), 3.70–3.60 (m, 2H), 3.20–3.00 (m, 3H), 2.37 (s, 3H), 1.46 (broad s, 3H), 1.40 (broad s, 3H). $^{13}$C NMR (DMSO-d$_6$), δ: 148.66, 147.93, 135.00, 129.21, 127.40, 125.40, 122.97, 121.82, 119.07, 113.56, 111.95, 111.24, 110.34, 57.32, 55.43, 55.33, 54.60, 36.46, 32.56, 21.24, 17.06, 15.92. IR (KBr): 3438, 2936, 1518, 1464, 1265, 1242, 1040 cm$^{-1}$. MS (EI): 365 (M$^+$-Cl, 100).

EXAMPLE 20

Cis-3-(2-amine-cyclohexyl)-5-methylindole, hydrochloride Cis-6-(3,4-dimethoxybenzyl)-10-methyl-2,3,4,4a,5,6,7,11c-octahydro-1H-indolo[2,3-c]quinoline, hydrochloride (4o)

The title compound (3i) was prepared following the procedure described by Scmuszkovicz, J. et al. *Tetrahedron*, 1991, 47, 8653 starting from 5-methylindole (1a).

Mp: 86°–90° C. $^1$H NMR (CD$_3$OD), δ: 7,38 (s, 1H), 7.26 (d, J=8.3 Hz, 1H), 7.11 (s, 1H), 6.96 (d, J=8.2, 1H), 3.90–3.70 (m, 1H), 3.55–3.38 (m, 1H), 2.42 (s, 3H), 2.40–2.35 (m, 1H), 2.10–1.79 (m, 4H), 1.75–1.50 (m, 3H). $^{13}$C NMR (CD$_3$OD), δ: 136.75, 129.27, 127.88, 124.63, 123.51, 118.71, 114.49, 112.34, 52.60, 36.79, 29.52, 26.44, 25.85, 21.68, 21.00. IR (KBr): 3401, 3017, 2932, 2863, 1561, 1489 cm$^{-1}$. MS (EI): 229 (M$^+$-Cl, 100).

The process for preparing the final product (4o) is illustrated by the following Scheme:

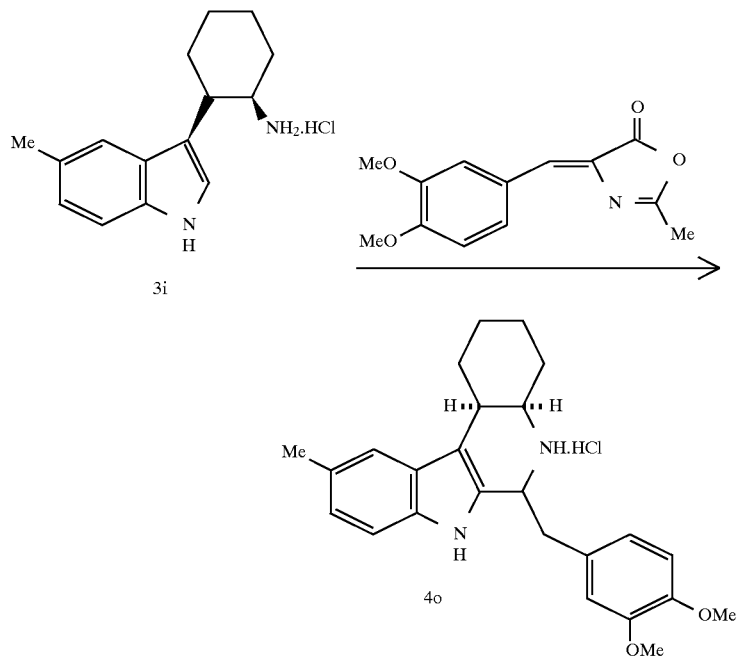

A suspension of the corresponding tryptamine hydrochloride (3h) (1 mmol) and 6,7-dimethoxytetralin-2-one (1.2 mmol) in 1N hydrochloric acid (3 ml.) was refluxed under Ar atmosphere during 72 h. After this time the reaction mixture was allowed to reach room temperature and filtered off. The crude solid was purified by flash chromatography using dichloromethane/methanol (9:1) as eluent.

Mp: 167°–171° C. $^1$H NMR (DMSO-d$_6$), δ: >11.0 (s, 1H), 8.87 (broad s, 2H), 7.29–7.20 (m, 3H), 7.12–6.85 (m, 3H), 4.95–4.80 (broad s, 1H), 3.76 (s, 3H), 3.75 (s, 3H), 3.70–3.60 (m), 3.25–3.00 (m, 1H), 2.36 (s, 3H), 2.40–2.00 (m), 1.95–1.20 (m, 6H), $^{13}$C NMR (DMSO-d$_6$), δ: 148.67 147.87, 134.80, 128.71, 128.43, 127.63, 125.45, 123.32, 121.75, 117.82, 113.59, 111.91, 111.30, 111.34, 56.99, 55.46, 55.12, 36.12, 36.65, 28.42, 27.49, 24.94, 24.39, 21.23, 19.17. IR (KBr): 3439, 2934, 1516, 1263 cm$^{-1}$. MS (EI): 390 (M$^+$-ClH, 100).

As noted above, the compounds of the present invention are useful in blocking the effect of serotonin or other agonists at 5-HT$_{2A}$, 5-HT$_{2B}$ and/or 5-HT$_{1c}$ receptors. Thus, the present invention also provides a method for blocking 5-HT$_{2A}$, 5-HT$_{2B}$ or 5-HT$_{1c}$ receptors in mammals comprising administering to a mammal requiring blocking of a 5-HT$_{2A}$, 5-HT$_{2B}$ or 5-HT$_{1c}$ receptor, respectively, a receptor blocking dose of a compound of the invention.

The term "receptor blocking dose", means an amount of compound necessary to block a targeted receptor, selected from the group consisting of 5-HT$_{2A}$, 5-HT$_{2B}$, and 5-HT$_{1c}$ receptor in a mammal. The active compounds are effective over a wide dosage range. For example, dosages per day will normally fall within the range of about 0.05 to about 250 mg/kg of body weight. In the treatment of adult humans, the range of about 0.5 to 100 mg/kg, in single or divided doses, is preferred. The ranges of about 5 mg/kg to about 60 mg/kg and about 10 mg/kg to about 50 mg/kg are especially preferred. However, it will be understood that the amount of the compound actually administered will be determined by a physician in light of the relevant circumstances, including the condition to be treated, the choice of compound to be administered, the age, weight, and response of the individual patient, the severity of the patient's symptoms, and the chosen route of administration, and therefore the above dosage ranges are not intended to limit the scope of the invention in any way. The compounds may be administered by a variety of routes such as oral, transdermal, subcutaneous, intranasal, intramuscular, and intravenous routes.

A variety of physiologic functions have been shown to be subject to be influenced by 5-HT$_{1c}$ receptors. Therefore, the compounds of the present invention can be used to treat a variety of disorders in mammals associated with these receptors. Such disorders include sleeping disorders, eating disorders, including bulimia and obesity, thermoregulation, sexual disorders, hyperactivity, excessive aggression, alcoholism, anxiety, obsessive-compulsive disorders, depression, schizophrenia and schizophreniform disorders, panic disorders, Gilles de la Tourette syndrome, migraine headaches, and Alzheimer's Disease. Additionally, effects of the 5-HT$_{1c}$ receptor indicate that the compounds of the present invention can be useful for relieving the sensation of pain. Thus, the present invention also provides methods for treating the above disorders and for relieving the sensation of pain.

Several examples of more specific disorders which may be treated using compounds of this invention include, but are not limited to: (numerals in parenthesis refer to the DSM-III-R Classification Codes) Attention-deficit hyperactivity disorder (314.01) conduct disorders (312.20, 312.00, 312.90), primary degenerative dementia of the Alzheimer type, senile onset (290.30, 290.20, 290.21, 290.00), primary degenerative dementia of the Alzheimer type, presenile onset (290.11, 290.12, 290.13, 290.10), alcohol withdrawal delirium (291.00), alcohol hallucinosis (291.30), alcohol, dementia associated with alcoholism (291.20), cannabis, delusional disorder (292.11), cocaine, intoxication (305.60), hallucinogen, mood disorder (292.84), nicotine withdrawal (292.00), phencyclidine or similarly acting arylcyclohexylamine intoxication (305.90), other psychoactive substance intoxication (305.90), delirium (293.00), dementia (294.10), organic delusional disorder (293.81), organic hallucinosis (293.82), organic mood disorder (293.83), organic anxiety disorder (294.80), organic personality disorder (310.10), organic mental disorder (294.80), schizophrenia, catatonic (295.21, 295.22, 295.23, 295.24, 295.25, 295.20), schizophrenia, disorganized (295.11, 295.12, 295.13, 295.14, 295.15, 295.00), schizophrenia, paranoid (295.31, 295.32, 295.33, 295.34, 295.35, 295.00), schizophrenia, undifferentiated (295.91, 295.92, 295.93, 295.94, 295.95, 295.00), schizophrenia, residual (295.61, 295.62, 295.63, 295.64, 295.65, 295.60), delusional (paranoid disorder (297.10), schizophreniform disorder (295.40), schizoaffective disorder (295.70), induced psychotic disorder (297.30), bipolar disorder, mixed (296.61, 296.62, 296.63, 296.64, 296.65, 296.66, 296.60), bipolar disorder, manic (296.41, 296.42, 296.43, 296.44, 296.45, 296.46, 296.40), bipolar disorder, depressed (296.51, 296.52, 296.53, 296.54, 296.55, 296.56, 296.50), major depression, single episode (296.21, 296.22, 296.23, 296.24, 296.25, 296.26, 296.20), major depression, recurrent (296.31, 296.32, 296.33, 296.34, 296.35, 296.36, 296.30), obsessive compulsive disorder (300.30), post-traumatic stress disorder (309.89), generalized anxiety disorder (300.02), hypochondriasis (300.07), somatization disorder (300.81), male erectile disorder (302.72), intermittent explosive disorder (312.34), impulse control disorder (312.39), paranoid (301.00), schizoid (301.20), schizotypal (301.22), antisocial (301.70), and borderline (301.83). *Diagnostic and Statistical Manual of Mental Disorders*, 3rd Ed. Revised, (1980), prepared by the Task Force on Nomenclature and Statistics of the American Psychiatric Association.

The compounds of the present invention have been found to display activity in a 5-HT$_{1c}$ receptor binding assay which measures the affinity of the compounds to bind to 5-HT$_{1c}$ receptors. The assays were conducted by the following procedures.

I. Assay for 5-HT$_{1c}$ Affinity

5-HT$_{1c}$ selective compounds can be identified using the following biological assay procedures. Compounds having a selective affinity for the 5-HT$_{1c}$ receptor have a low IC$_{50}$ in the 5-HT$_{1c}$ receptor assay and a higher IC$_{50}$ in the 5-HT$_2$ receptor assay. As shown by Table II (below) the compounds prepared in Examples 3, 4, 6, 7, 10, 13, 15, and 16 are particularly 5-HT$_{1c}$ selective.

IA. Biological Reagent Preparation

Beef brain was removed immediately after slaughter, and choroid plexus were dissected over ice. Male Sprague-Dawley rats weighing 125–150 g (Harlan Industries, Cumberland, Ind.) were killed by decapitation. The brain of each was immediately removed and the cerebral cortex was dissected over ice. Tissues were homogenized in 9 volumes of 0.32 mol/L sucrose and centrifuged at 1,000×g for 10 minutes. The supernatant was centrifuged at 17,000×g for 20 minutes. The pellet was suspended in 100 volumes of 50 mM Tris-HCl (pH 7.4), incubated at 37° C. for 10 minutes and centrifuged at 50,000×g for 10 minutes, and the process was repeated three times. The final pellets were frozen at −70° C. and used within 2 weeks. Pellets were rehydrated with physiological buffer prior to use.

II. Assay Procedure

Radioligand binding assays for 5-HT$_{1c}$ and 5-HT$_2$ receptors were conducted according to described methods. The assays can be conducted as described by Hoyer D., Functional correlates of serotonin 5-HT$_1$ recognition sites, *J. Receptor Res* 8, 59–81 (1988) and Hoyer D., Engel G., Kalkman H. O. Molecular pharmacology of 5-HT$_1$ and 5-HT$_2$ recognition sites in rat and pig brain membranes: Radio-ligand binding studies with [$^3$H]5-HT, [$^3$H]8-OH-DPAT, (−) [$^{125}$I] iodocyanopindolol, [$^3$H]mesulergine and [$^3$H]ketanserin, *Eur. J. Pharmacol.* 118, 13–23 (1985).

For 5-HT$_{1c}$ receptor assays increasing concentrations of experimental compound, 50 mM Tris HCl buffer pH 7.4, and tritiated mesulergine (2.0 nM) ($^3$H ligand) were combined in polystyrene tubes at room temperature. The reaction was initiated by the addition of the resuspended choroid plexus tissue which had been preincubated at 37° C. for 20 minutes. The reaction mixture was incubated in a 37° C. water bath for 15 minutes.

For 5-HT$_{2B}$ receptor assays increasing concentrations of experimental compound, 50 mM Tris HCl buffer pH 7.4, and tritiated ketanserin (1 nM) ($^3$H ligand) were combined in polystyrene tubes at room temperature. The reaction was initiated by the addition of the resuspended rat cerebral cortex tissue which had been preincubated at 37° C. for 20 minutes. The reaction mixture was incubated in a 37° C. water bath for 30 minutes.

The reactions were terminated by rapid filtration, (Brandel Cell Harvestor), through Whatman GF/B glass filters that had been presoaked in Tris buffer pH 7.4. The filters were then washed 2 times with 5 ml of ice cold Tris buffer pH 7.4. Washed filters were placed in scintillation vials and 10 ml RedySolv, (Brandel), was added and samples were counted in a Searle D-300 beta counter. Means and standard error statistics were calculated for triplicate experimental determinations in certain cases. Mean values were obtained from three or more separate determinations. The incubation time for the reaction mixture was 15 minutes at 37° C.

Concentrations that caused a 50% inhibition of radioligand binding (IC$_{50}$) and Hill coefficient were obtained by computer-assisted regression analysis.

One particularly useful embodiment of this invention is that it provides selective ligands for the 5-HT$_{2B}$ receptor. Compounds with a high affinity for the 5-HT$_{2B}$ receptor generally are cross-reactive with the 5-HT$_{2C}$ receptor as well. Now 5-HT$_{2B}$ receptors can be selectively modulated using compounds of this invention at rates set forth above for blocking the effects of agonists at 5-HT$_{2B}$ receptors. The selective affinity may provide treatments with fewer side effects and will facilitate the development of additional therapeutic agents.

Certain compounds and intermediates of the present invention are useful for modulating 5-HT$_{2B}$ receptors. The compounds which are most useful for binding a 5HT$_{2B}$ receptor can be identified using the following procedures. Further, a useful in vivo model for demonstrating 5-HT$_{2B}$ activity is provided infra.

II. Radioligand Binding Studies for 5-HT$_{2B}$

Membrane preparation from transformed cells. Suspension cells expressing the cloned rat 5-HT$_{2B}$ receptor were harvested by centrifugation at 2,200×g for 15 min at 4° C. Kursar, J. D., D. L. Nelson, D. B. Wainscott, M. L. Cohen, and M. Baez, *Mol. Pharmacol.*, 42: 549–557 (1992). Membranes for the binding assays were prepared by vortexing the pellet in 50 mM Tris-HCl, pH 7.4 (0.5×10$^9$ cells/30 ml). The tissue suspension was then centrifuged at 39,800×g for 10 min at 4° C. This procedure was repeated for a total of three washes, with a 10 minute incubation at 37° C. between the first and second wash. The final pellet was homogenized in 67 mM Tris-HCl, pH 7.4 (at 20–40 and 12.5 million cells/ml, original cell number, for cells expressing low and relatively high levels of the 5-HT$_{2B}$ receptor, respectively) using a Tissumizer (Tekmar, Cincinnati, Ohio), setting 65 for 15 seconds.

[$^3$H]5-HT binding studies. Binding assays were automated using a Biomek 1000 (Beckman Instruments, Fullerton, Calif.) and were performed in triplicate in 0.8 ml total volume. Membrane suspension, 200 μl, (0.04–0.27 mg protein) and 200 μl of drug dilution in water were added to 400 μl of 67 mM Tris-HCl, pH 7.4, containing [3H]5-HT, pargyline, CaCl$_2$, and L-ascorbic acid. Final concentrations of pargyline, CaCl$_2$ and L-ascorbic acid were 10 μM, 3 mM and 0.1%, respectively. Tubes were incubated at 37° C. for 15 min or at 0° C. for 2 hours (binding equilibria were verified for both of these conditions), then rapidly filtered using a Brandel cell harvester (Model MB-48R; Brandel, Gaithersburg, Md.) through Whatman GF/B filters which had been presoaked in 0.5% polyethylenimine and pre-cooled with ice-cold 50 mM Tris-HCl, pH 7.4. The filters were then washed rapidly four times with one ml ice-cold 50 mM Tris-HCl, pH 7.4. The amount of [$^3$H]5-HT trapped on the filters was determined by liquid scintillation spectrometry (Ready Protein and Beckman LS 6000IC, Beckman Instruments, Fullerton, Calif.). For the saturation experiments, actual free radioligand concentrations were determined by sampling the supernatant of parallel saturation experiments in which bound radioactivity had been separated by centrifugation. The concentration of [$^3$H]5-HT ranged from 0.02 to 5 nM and 0.6 to 63 nM for saturation experiments incubated at 0° C. and 37° C., respectively. 5-HT, 10 μM, or 1-naphthylpiperazine (1-NP), 10 μM, defined nonspecific binding. For competition experiments, six to twelve concentrations of displacing drugs were used, spanning six log units, and the final concentration of [$^3$H] 5-HT was 2 nM. Protein was determined by the method of Bradford, using bovine serum albumin as the standard. Bradford, M. M., *Anal. Biochem.* 72: 248–254 (1976).

Statistical Analysis

The K$_d$ and B$_{max}$ values from the saturation assays were determined for best fit to a one-site or a two-site binding model using a partial F-test. De Lean, A., A. A. Hancock, and R. J. Lefkowitz, *Mol. Pharmacol.* 21: 5–16 (1981). The following equation was used for a one-site binding model, $$\text{Bound} = \frac{B_{max} \times [L]}{K_d + [L]}$$

where Bound=amount of [$^3$H]5-HT specifically bound, B$_{max}$=maximum number of binding sites, K$_d$=equilibrium dissociation constant and [L]=free concentration of [$^3$H]5-HT, or a two-site binding model, $$\text{Bound} = \frac{B_{max1} \times [L]}{K_{d1} + [L]} + \frac{B_{max2} \times [L]}{K_{d2} + [L]}$$

where Bound=amount of [$^3$H]5-HT specifically bound, B$_{max1}$=maximum number of high affinity binding sites, B$_{max2}$=maximum number of low affinity binding sites, K$_{d1}$=equilibrium dissociation constant for the high affinity site, K$_{d2}$=equilibrium dissociation constant for the low affinity site and [L]=free concentration of [$^3$H]5-HT. The IC$_{50}$ values from the competition assays, the binding parameters for the IP$_3$ standard curve and the EC$_{50}$ and E$_{max}$ values from the IP$_3$ assays were determined by nonlinear regression analysis of four parameter logistic equations (Systat, Systat Inc, Evanston, Ill.). De Lean, A., A. A. Hancock, and R. J. Lefkowitz, *Mol. Pharmacol.*, 21: 5–16 (1981). The IC$_{50}$ values were converted to $K_i$ values using the Cheng-Prusoff equation. Cheng, Y., and W. H. Prusoff, *Biochem. Pharmacol.*, 22: 3099–3108 (1973).

TABLE I

The following Cell assays use Human Cells

| Compound | $5HT_{2B}$ Cells | $5HT_{2A}$ Cells | $5HT_{2C}$ Cells |
|---|---|---|---|
| Example 11 | 16.44 | 292.58 | 351.96 |
| Example 15 | 22.07 | 86.48 | 195.44 |
| Example 13 | 168.49 | 917.16 | 2172.86 |
| Example 17 | 367.41 | 263.94 | 1108.87 |
| Example 15 | 11.35 | 32.99 | 52.06 |
| Example 8 | 9.56 | 123.93 | 220.51 |
| Example 10 | 106.17 | 556.40 | 1117.00 |
| Example 18 | 177.89 | 362.79 | 325.10 |
| Isomer 18(1) | 142.80 | 152.65 | 137.76 |
| Isomer 18(2) | 2894.33 | 1967.05 | 6211.80 |
| Example 12 | 121.19 | 172.03 | 783.35 |
| Example 9 | 52.54 | 53.65 | 202.60 |
| Example 7 | 667.82 | 277.62 | 976.73 |
| Example 6 | 839.63 | 3443.51 | 2641.21 |
| Example 14 | 3520.31 | 1447.65 | 9247.06 |

III. Assay Methods $5\text{-}HT_{2B}$ in vitro

Male Wistar rats (150–375 g; Laboratory Supply, Indianapolis, Ind.) were sacrificed by cervical dislocation, and longitudinal section of the stomach fundus were prepared for in vitro examination. Four preparations were obtained from one rat fundus. Ring preparations of the extracted jugular vein were prepared as described by Hooker; *Blood Vessels* 14:1 (1977) and Cohen, M. L. *J. Pharamcol. Exp. Ther.* 227:327 (1983). Tissues were mounted in organ baths containing 10 mL of modified Krebs solution of the following composition (millimolar concentrations): NaCl, 118.2; KCl, 4.6; $CaCl_2.H_2O$, 1.6; $KH_2PO_4$, 1.2; $MgSO_4$, 1.2; dextrose, 10.0; and $NaHCO_3$, 24.8. Tissue bath solutions were maintained at 37° C. and equilibrated with 95% $O_2$ and 5% $CO_2$. Tissues were placed under optimum resting force (4 g) and were allowed to equilibrate for approximately 1 hour before exposure to the test compound. Isometric contractions were recorded as changes in grams of force on a Beckman Dynograph with Statham UC-3 transducers.

Determination of Apparent Antagonist Dissociation Constant

Noncumulative contractile concentration-response curves for serotonin in the fundus and cumulatative concentration response curves in the jugular vein were obtained by a stepwise increase in concentration after washing out the preceding concentrations every 15–20 minutes. Each agonist concentration remained in contact with the tissue for approximately 2 minutes and maximum response to each compound concentration was measured. $ED_{50}$ values were taken as the concentration of agonist that produced half-maximal contraction. After control responses were obtained, tissues were incubated with an appropriate concentration of buffer or antagonist for 1 hour. Responses to serotonin were then repeated in the presence of an antagonist. Concentration responses utilized only one agonist and one antagonist concentration per tissue. In general, successive agonist responses in the presence of buffer treatment were unaltered (average dose ratio was 1.28±0.21).

Apparent antagonist dissociation constants ($K_B$) were determined for each concentration of antagonist according to the following equation:

$$K_B=[B]/(\text{dose ratio}-1)$$

where [B] is the concentration of the antagonist and dose ratio is the $ED_{50}$ of the agonist in the presence of the antagonist divided by the control $ED_{50}$. Generally, parallel shifts in the concentration-response curves occurred in the presence of antagonists. The results were expressed as the negative logarithm of the $K_B$ (i.e., $-\log K_B$). Calculations were completed using known methods. Zaborowsky, B. R. *J. Pharmacol. Methods* 4:4165 (1980).

Compounds of this invention were tested and demonstrated $5\text{-}HT_{2B}$ receptor activity using this described in vitro method.

In vivo Studies

Sprague-Dawley Rats (250–300 g) were fasted overnight. The rats were anesthetized with urethane (250 mg) delivered intraperitoneally. The abdominal cavity was opened and strain guage transducers were sewn on the antimesenteric border of the colon. The transducers were oriented to record circular muscle contractions. The animal body temperature was maintained by a heating pad. An intravenous catheter was inserted into the jugular vein for drug administration. The carotid blood pressure was also monitored. Output of the strain guage transducers was graphed on a Beckman Dynograph. Baseline motility was monitored for 30 minutes. At the end of the 30 minute period, a vehicle control dose was administered and motility was recorded for an additional 15 minutes. A serotonin dose response was developed. Successively higher doses of serotonin were administered at 15 minute intervals. An $ED_{50}$ dose was calculated, which was the dose producing half maximal contraction. In antagonist experiments, historical $ED_{50}$ dose was administered to validate the experimental set up. Next, a dose of antagonist was given. The motility was monitored for 15 minutes. After the 15 minute monitoring, an $ED_{50}$ dose was administered. Motility was evaluated by measuring the number of contractions and multiplying them by the amplitude of contractions over a set time period to provide a Motility Index. The percent inhibition was calculated from the vehicle (no antagonist) treated group. A minimum of three rats were used for each concentration and data from different animals was pooled to determine $ED_{50}$ values.

Compounds exhibiting activity at the $5HT_{2B}$ receptor are useful for treating disorders related to the modulation of the $5HT_{2B}$ receptor. For example, compounds having $5HT_{2B}$ antagonist activity reduce the spasticity of the colon. Thus, these compounds are useful for the treatment of functional bowel disorders including irritable bowel syndrome and irritable bowel syndrome-related symptoms. The antispasmodic effect of such compounds can reduce abdominal pain associated with functional bowel disorders. Additionally, the $5HT_{2B}$ receptor is localized in other organs such as the brain, bladder, blood vessels, stomach, and uterus, indicating that additional conditions are $5HT_{2B}$ mediated.

Compounds demonstrating activity at the $5HT_{2A}$ receptor can be utilized in the treatment or prevention of conditions related to modulation of the $5HT_{2A}$ receptor. Examples of such conditions include hypertension, sleep disorders, hallucinogenic activity, psychosis, anxiety, depression, thermoregulation, feeding disorders, and hypotension. Leonard, B. E., *International Clinical Psychopharmacology*, 7, 13–21 (1992).

While it is possible to administer a compound of the invention directly without any formulation, the compounds are preferably employed in the form of a pharmaceutical formulation comprising a pharmaceutically acceptable excipient and at least one compound of the invention. Such compositions contain from about 0.1 percent by weight to about 90.0 percent by weight of a present compound. As such, the present invention also provides pharmaceutical formulations comprising a compound of the invention and a pharmaceutically acceptable excipient therefor.

In making the compositions of the present invention, the active ingredient is usually mixed with an excipient which can be a carrier, or a diluent or be diluted by a carrier, or enclosed within a carrier which can be in the form of a capsule, sachet, paper or other container. When the carrier serves as a diluent, it can be a solid, semi-solid, or liquid material which acts as a vehicle, excipient, or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

The compounds of the invention may be delivered transdermally, if desired. Transdermal permeation enhancers and delivery systems, including patches and the like, are well known to the skilled artisan.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxy- benzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The compounds of this invention may be delivered transdermally using known transdermal delivery systems and excipients. Most preferrably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For oral administration, a compound of this invention ideally can be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect in association with a suitable pharmaceutical carrier.

In order to more fully illustrate the operation of this invention, the following formulation examples are provided. The examples are illustrative only, and are not intended to limit the scope of the invention. The formulations may employ as active compounds any of the compounds of the present invention.

Formulation 1

Hard gelatin capsules are prepared using the following ingredients:

|  | Amount Per Capsule | Concentration by Weight (percent) |
|---|---|---|
| Trans-9-methyl-5-(1-naphthylmethyl)-1,2,3,4-4a,5,6,10c,octahydrocyclopenta[a]pyrido[3,4-b]indole, hydrochloride | 250 mg | 55.0 |
| starch dried | 200 mg | 43.0 |
| magnesium stearate | 10 mg | 2.0 |
|  | 460 mg | 100.0 |

The above ingredients are mixed and filled into hard gelatin capsules in 460 mg quantities.

Formulation 2

Capsules each containing 20 mg of medicament are made as follows:

|  | Amount Per Capsule | Concentration by Weight (percent) |
|---|---|---|
| spiro-6,6[2-(3,5-dimethoxy)-1,2,3,4-tetrahydronaphthyl]-10-methyl-2,3,4,4a,5,6,7,11a-octahydro-1H-indolo[2,3-c]-quinuclidine, hydrochloride | 20 mg | 10.0 |
| starch | 89 mg | 44.5 |
| microcrystalline cellulose | 89 mg | 44.5 |
| magnesium stearate | 2 mg | 1.0 |
|  | 200 mg | 100.0 |

The active ingredient, cellulose, starch, and magnesium stearate are blended, passed through a No. 45 mesh U.S. sieve and filled into a hard gelatin capsule.

Formulation 3

Capsules each containing 100 mg of medicament are made as follows:

|  | Amount Per Capsule | Concentration by Weight (percent) |
|---|---|---|
| spiro-6,6[2-(3-fluoro-4-methoxy)-1,2,3,4-tetrahydronaphthyl]-10-methyl-2,3,4,4a,5,6,7,11a-octahydro-1H-indolo[2,3-c]-quinuclidine, hydrochloride | 100 mg | 30.00 |
| polyoxyethylene sorbitan monooleate | 50 mg | 0.02 |
| starch powder | 250 mg | 69.98 |
|  | 350 mg | 100.00 |

The above ingredients are thoroughly mixed and placed in an empty gelatin capsule.

Formulation 4

Tablets containing 10 mg of active ingredient are made as follows:

| | Amount Per Tablet | Concentration by weight (percent) |
|---|---|---|
| 8-fluoro-10-phenoxy-6-(1-naphthylmethyl)-2,3,4,4a,5,6,7,11c-octahydro-1H-indolo-[2,3-c]quinoline, tartrate | 10 mg | 10.0 |
| starch | 45 mg | 45.0 |
| microcrystalline cellulose | 35 mg | 35.0 |
| polyvinylpyrrolidone (as 10% solution in water) | 4 mg | 4.0 |
| sodium carboxymethyl starch | 4.5 mg | 4.5 |
| magnesium stearate | 0.5 mg | 0.5 |
| talc | 1 mg | 1.0 |
| | 100 mg | 100.0 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50°–60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

Formulation 5

A tablet formulation may be prepared using the ingredients below:

| | Amount Per Tablet | Concentration by Weight (percent) |
|---|---|---|
| 8-methyl-10-methoxy-6-(1-naphthylethyl)-2,3,4,4a,5,6,7,11c-octahydro-1H-indolo-[2,3-c]quinoline | 250 mg | 38.0 |
| microcrystalline cellulose | 400 mg | 60.0 |
| silicon dioxide fumed | 10 mg | 1.5 |
| stearic acid | 5 mg | 0.5 |
| | 665 mg | 100.0 |

The components are blended and compressed to form tablets each weighing 665 mg.

Formulation 6

Suspensions each containing 5 mg of medicament per 5 ml dose are as follows:

| | per 5 ml of suspension |
|---|---|
| 8-chloro-10-cyclopropyl-6-(1-naphthylethyl)-2,3,4,4a,5,6,7,11c-octahydro-1H-indolo-[2,3-c]quinoline | 5 mg |
| sodium carboxymethyl cellulose | 50 mg |
| syrup | 1.25 ml |
| benzoic acid solution | 0.10 ml |
| flavor | q.v. |
| color | q.v. |
| water | q.s. to 5 ml |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

| | Concentration by Weight (percent) |
|---|---|
| spiro-6,6[2-(3-ethyl-4-ethoxy)-1,2,3,4-tetrahydronaphthyl]-10-methyl-2,3,4,4a,5,6,7,11a-octahydro-1H-indolo[2,3-c]-quinuclidine, maleate | 0.25 |
| ethanol | 29.75 |
| Propellant 22 (chlorodifluoromethane) | 70.00 |
| | 100.00 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

Formulation 8

A tablet formulation may be prepared using the ingredients below:

| | Amount Per Tablet | Concentration by Weight (percent) |
|---|---|---|
| spiro-6,6[2-(3-ethyl-4-ethoxy)-1,2,3,4-tetrahydro-6-methyl-naphthyl]-10-methyl-2,3,4,4a,5,6,7,11a-octahydro-1H-indolo[2,3-c]-quinuclidine, maleate | 250 mg | 38.0 |
| microcrystalline cellulose | 400 mg | 60.0 |
| silicon dioxide fumed | 10 mg | 1.5 |
| stearic acid | 5 mg | 0.5 |
| | 665 mg | 100.0 |

The components are blended and compressed to form tablets each weighing 665 mg.

We claim:
1. A compound of formula I:

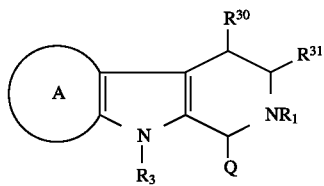

wherein:
Q is $R_{34}$; $R_{34}$ is spirobicyclic or substituted spirobicyclic;
$R_1$ and $R_3$, independently, are hydrogen or $C_1$–$C_3$ alkyl;
$R_2$ is hydrogen or $C_1$–$C_6$ alkyl;
A is

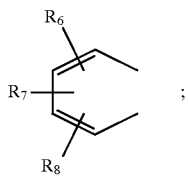

$R_6$ and $R_7$, independently, are hydrogen, $C_1$–$C_6$ alkyl, $C_2$–$C_6$ alkenyl, halo, halo ($C_1$–$C_6$) alkyl, halo($C_2$–$C_6$) alkenyl, $COR_5$, $C_1$–$C_{10}$ alkanoyl, $CO_2R_{5'}$, ($C_1$–$C_6$ alkyl)$_m$amino, $NO_2$, —$SR_5$ or $OR_5$; or
$R_6$ and $R_7$ together with the carbon atoms of group A form a 5- to 8-member carbon ring;

$R_8$ is an $R_6$ group, $C_3$–$C_8$ cycloalkyl, substituted $C_3$–$C_8$ cycloalkyl, $C_3$–$C_8$ cycloalkyl($C_1$–$C_3$)alkyl, phenyl, substituted phenyl, $C_5$–$C_8$ cycloalkenyl, substituted $C_5$–$C_8$ cycloalkenyl, phenyl-($C_1$–$C_3$)alkyl, $C_5$–$C_8$ cycloalkenyl-($C_1$–$C_3$)alkyl, or $C_7$–$C_{16}$ arylalkyl;

m is 1 or 2;

$R_5$ is hydrogen or $C_1$–$C_4$ alkyl;

$R_{5'}$ is $C_1$–$C_4$ alkyl; and $R_{30}$ and $R_{31}$, independently, are $C_1$–$C_6$ alkyl or $C_2$–$C_6$ alkenyl; or a pharmaceutically acceptable salt or solvate thereof.

2. A pharmaceutical formulation comprising a compound of claim 1 and one or more pharmaceutically acceptable excipients therefor.

3. A method for treating a mammal suffering from or susceptible to a condition associated with $5HT_{2B}$ modulation, which comprises administering to said mammal an effective amount of a compound of claim 1.

4. A method of claim 3 for treating a mammal suffering from, or susceptible to a Functional Bowel Disorder.

5. A method of claim 3 for selectively binding 5-$HT_{2B}$ receptors in mammals comprising administering to a mammal requiring selective binding of a 5-$HT_{2B}$ receptor, a receptor binding dose wherein the compound selectively binds 5-$HT_{2B}$ receptors.

* * * * *

UNITED STATES PATENT AND TRADEMARK OFFICE
CERTIFICATE OF CORRECTION

PATENT NO. : 5,861,408
DATED : January 19, 1999
INVENTOR(S) : James E. Audia, et al.

It is certified that error appears in the above-identified patent and that said Letters Patent is hereby corrected as shown below:

In column 22, line 63, please delete "quinidine" and insert therefor --quinoline--.

In column 32, line 30, please delete "quinuclidine" and insert therefor --quinoline--.

In column 32, line 48, please delete "quinuclidine" and insert therefor --quinoline--.

In column 34, line 32, please delete "quinuclidine" and insert therefor --quinoline--.

In column 34, line 58, please delete "quinuclidine" and insert therefor --quinoline--.

Signed and Sealed this

Twentieth Day of June, 2000

Attest:

Q. TODD DICKINSON

*Attesting Officer*     *Director of Patents and Trademarks*